United States Patent
Li et al.

(10) Patent No.: US 9,314,648 B2
(45) Date of Patent: Apr. 19, 2016

(54) SYSTEM, METHOD AND APPARATUS FOR TRACKING TARGETS DURING TREATMENT USING A RADAR MOTION SENSOR

(71) Applicant: Texas Tech University System, Lubbock, TX (US)

(72) Inventors: Changzhi Li, Lubbock, TX (US); Changzhan Gu, Lubbock, TX (US)

(73) Assignee: Texas Tech University System, Lubbock, TX (US)

( * ) Notice: Subject to any disclaimer, the term of this patent is extended or adjusted under 35 U.S.C. 154(b) by 468 days.

(21) Appl. No.: 13/726,199

(22) Filed: Dec. 23, 2012

(65) Prior Publication Data
US 2013/0165770 A1  Jun. 27, 2013

Related U.S. Application Data

(60) Provisional application No. 61/579,971, filed on Dec. 23, 2011.

(51) Int. Cl.
| | |
|---|---|
| A61B 5/05 | (2006.01) |
| A61N 5/10 | (2006.01) |
| A61N 5/06 | (2006.01) |
| A61B 5/11 | (2006.01) |
| A61B 5/113 | (2006.01) |

(52) U.S. Cl.
CPC ............ *A61N 5/1067* (2013.01); *A61B 5/0507* (2013.01); *A61B 5/113* (2013.01); *A61B 5/1127* (2013.01); *A61N 5/0613* (2013.01); *A61N 5/1049* (2013.01); *A61N 2005/0626* (2013.01)

(58) Field of Classification Search
USPC ......................................................... 600/430
See application file for complete search history.

(56) References Cited

U.S. PATENT DOCUMENTS

| | | | | |
|---|---|---|---|---|
| 4,600,892 | A | * | 7/1986 | Wagner et al. ................. 330/144 |
| 5,657,760 | A | | 8/1997 | Ying et al. |
| 5,731,781 | A | * | 3/1998 | Reed .............................. 342/135 |
| 5,769,879 | A | * | 6/1998 | Richards et al. .............. 607/101 |
| 6,298,260 | B1 | | 10/2001 | Sontag et al. |

(Continued)

OTHER PUBLICATIONS

Ghovanloo et al. (A wide-band power-efficient inductive wireless link for implantable microelectronic devices using multiples carriers, 2007).*

(Continued)

*Primary Examiner* — Joel F Brutus
(74) *Attorney, Agent, or Firm* — Daniel J. Chalker; Edwin S. Flores; Chalker Flores, LLP

(57) ABSTRACT

A system, method and apparatus tracks targets (e.g., tumors) during treatment (e.g., radiation therapy) using a radar motion sensor by generating a microwave signal, radiating the microwave signal to a subject, and receiving a modulated microwave signal from the subject. The modulated microwave signal is processed to provide a subject motion information using a sensor having an arctangent-demodulation microwave interferometry mode. A location of a target on or within the subject is determined based on the subject motion information and a three-dimensional model for the subject and the target. One or more control signals are generated based on the location of the target, and the treatment device is controlled using the one or more control signals to treat the target on or within the subject.

61 Claims, 13 Drawing Sheets

(56) References Cited

U.S. PATENT DOCUMENTS

| | | | |
|---|---|---|---|
| 7,359,535 B2 | 4/2008 | Salla et al. | |
| 7,756,565 B2 | 7/2010 | Salla et al. | |
| 7,778,691 B2 | 8/2010 | Zhang et al. | |
| 7,844,317 B2 | 11/2010 | Salla et al. | |
| 2003/0088180 A1* | 5/2003 | Van Veen et al. | 600/430 |
| 2004/0001541 A1* | 1/2004 | Haghighat | 375/232 |
| 2007/0093797 A1* | 4/2007 | Chan et al. | 606/12 |
| 2007/0135709 A1* | 6/2007 | Rioux et al. | 600/429 |
| 2008/0243018 A1 | 10/2008 | Zuhars et al. | |
| 2008/0272959 A1* | 11/2008 | Meharry et al. | 342/174 |
| 2009/0196480 A1* | 8/2009 | Nields et al. | 382/132 |
| 2010/0198083 A1* | 8/2010 | Lin et al. | 600/484 |

OTHER PUBLICATIONS

Li et al. (Complex signal demodulation and random body movement cancellation techniques for non-contact vital sign detection).*

Arslan, S., et al., "CT-guided transthoracic fine needle aspiration of pulmonary lesions: accuracy and complications in 294 patients," Med Sci Monit, vol. 8, No. 7, pp. 493-500, 2002.

Berbeco, R. I., et al., "Residual motion of lung tumors in end-of-inhale respiratory gated radiotherapy based on external surrogates", Med. Phys. vol. 33, No. 11, 2006.

Droitcour, A. D., et al., "Range correlation and I/Q performance benefits in single-chip silicon Doppler radars for noncontact cardiopulmonary monitoring," IEEE Trans. Microwave Theory and Techniques, vol. 52, No. 3, pp. 838-848, Mar. 2004.

Geraghty, P.R., et al., "CT-guided transthoracic needle aspiration biopsy of pulmonary nodules: needle size and pneumothorax rate," Radiology, 2003. 229(2): p. 475-481.

Gibson, S.F., "3D chainmail: a fast algorithm for deforming volumetric objects, in Proceedings of the 1997 symposium on Interactive 3D graphics," ACM: Providence, Rhode Island, 1997.

Gu, C., et al., "A multi-radar wireless system for respiratory gating and accurate tumor tracking in lung cancer radiotherapy", 33rd Annual International Conference of the IEEE Engineering in Medicine and Biology Society (EMBC '11), Boston MA, Aug. 2011.

Gu, C. et al., "Instrument-based noncontact Doppler radar vital sign detection system using heterodyne digital quadrature demodulation architecture," IEEE Transactions on Instrumentation and Measurement, vol. 59, No. 6, pp. 1580-1588, 2010.

Gu, c., et al., "Doppler Radar Respiration Measurement for Gated Lung Cancer Radiotherapy", IEEE Radio and Wireless Week, Phoenix AZ, Jan. 2011.

Jiang, S.B., "Technical aspects of image-guided respirationgated radiation therapy," Med Dosim, vol. 31, No. 2, pp. 141-151, 2006.

Jiang, S. B., "Radiotherapy of mobile tumors," Seminars in Radiation Oncology, vol. 16, Issue. 4, pp. 239-24, Oct. 2006.

Keall, P.J., et al., "Motion adaptive x-ray therapy: a feasibility study," Phys Med Biol, vol. 46, No. 1, pp. 1-10, 2001.

Kim, S., et al., "A displacement measurement technique using millimeter-wave interferometry," IEEE Trans. Microwave Theory and Techniques, vol. 51, No. 6, pp. 1724-1728, 2003.

Laurent, F.,et al, "CT-guided transthoracic needle biopsy of pulmonary nodules smaller than 20 mm results with an automated 20-gauge coaxial cutting needle", Clin. Radiol. vol. 55, pp. 281-287, 2000.

Li, C. et al., "Radar Motion Sensing for Accurate Tumor Tracking in Radiation Therapy", IEEE Wireless and Microwave Technology Conference, Clearwater Beach FL, Apr. 2011.

Li C., et al., "Radar remote monitoring of vital signs," IEEE Microwave Magazine, vol. 10, issue 1, pp. 47-56, Feb. 2009.

Lin, J. C., "Noninvasive microwave measurement of respiration", Proceedings of the IEEE, vol. 63, No. 10, pp. 1530-1530, Oct. 1975.

Mostafanezhad, I., et al., "An RF Based Analog Linear Demodulator", IEEE Microwave and Wireless Components Letters, vol. 21, No. 7, pp. 392-394, Jul. 2011.

Mostov, K., et al., "Medical Applications of Shortwave RM Radar: Remote Monitoring of Cardiac and Respiratory Motion," Medical Physics Online Journal, Mar. 2010.

Pan, W., et al., "Null point elimination using RF phase shifter in continuous wave Doppler radar system," Electronics Letter, vol. 47, No. 21, p. 1196-1198, Oct. 2011.

Park, B. K, et al., "Arctangent demodulation with DC offset compensation in quadrature Doppler radar receiver systems," IEEE Trans. Microwave Theory and Techniques, vol. 55, No. 5, pp. 1073-1079, May 2007.

Razavi, B., "Design Considerations for Direct-Conversion Receivers", IEEE Trans. Circuits & Systems I, vol. 44, No. 6, pp. 428-435, Jun. 1997.

Rice, J.A., etr al., "A wireless multifunctional radar-based displacement sensor for structural health monitoring," SPIE Smart Structures/NDE 2010, San Diego, CA, USA, Mar. 2011.

Shope, T.B., "Radiation-induced skin injuries from fluoroscopy," Radiographics, vol. 16, No. 5, pp. 1195-1199, 1996.

Wilson, T.A., et al., "Respiratory effects of the external and internal intercostal muscles in humans," J Physiol, vol. 530, pp. 319-349, 2001.

Xu, Q., et al., "Lung Tumor Tracking in Fluoroscopic Video Based on Optical Flow," Medical Physics, vol. 35, No. 12, pp. 5351-5359, 2008.

Zhao, X., et al. "DC Coupled Doppler Radar Physiological Monitor", 33rd Annual International Conference of the IEEE Engineering in Medicine and Biology Society (EMBC '11), Boston MA, Aug. 2011.

Murphy, M.J., "Tracking moving organs in real time," Semin Radiat Oncol, vol. 14, No. 1, pp. 91-100, 2004.

Shirato, H., et al., "Physical aspects of a realtime tumor-tracking system for gated radiotherapy," Int J Radiat Oncol Biol Phys, vol. 48, No. 4, pp. 1187-1195, 2000.

Lin, T., et al., "Fluoroscopic tumor tracking for image-guided lung cancer radiotherapy," Phys Med Biol, vol. 54, No. 4, pp. 981-992, 2009.

* cited by examiner

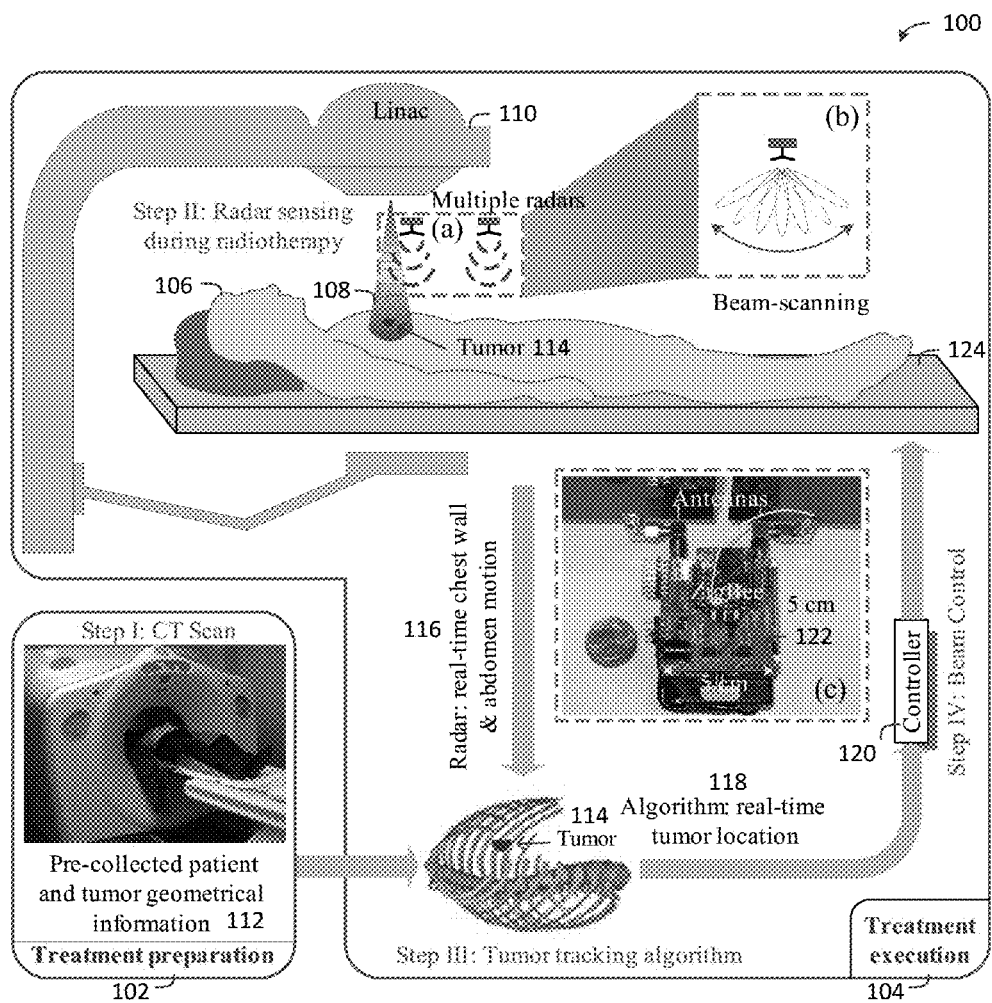
FIG. 1
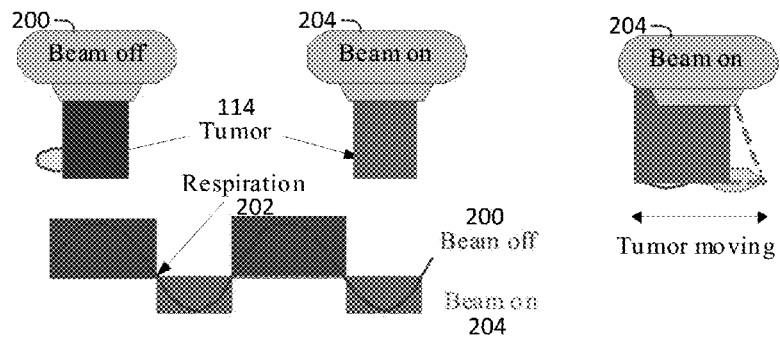
FIG. 2A
FIG. 2B

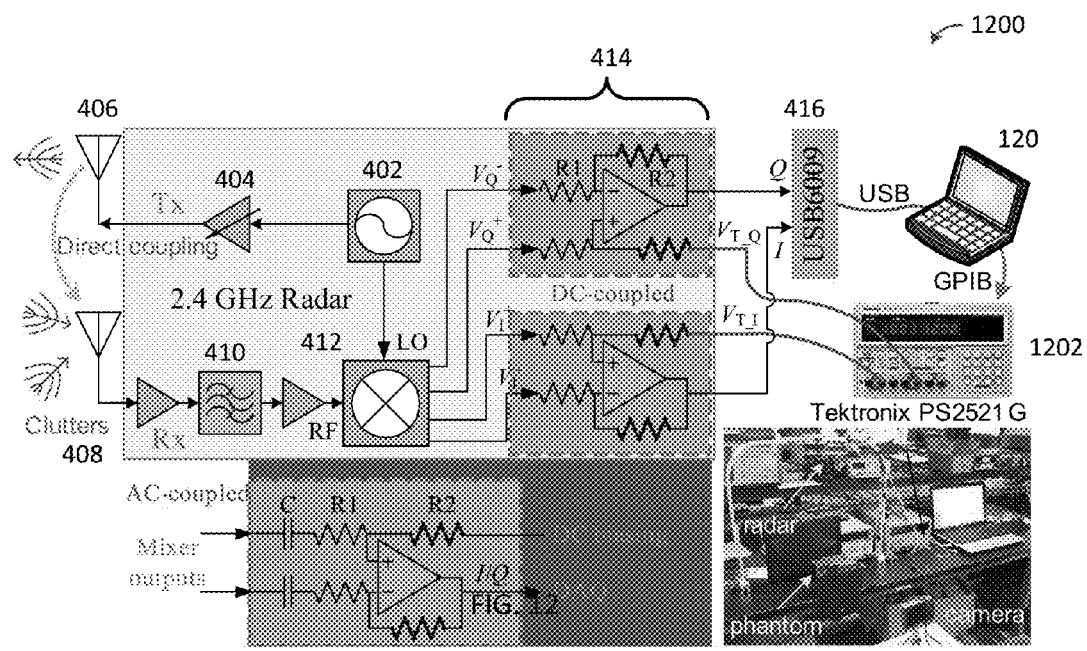
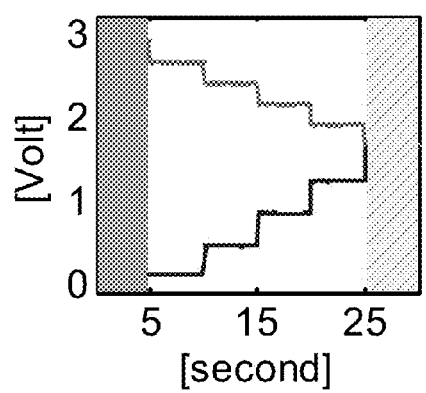
FIG. 13A
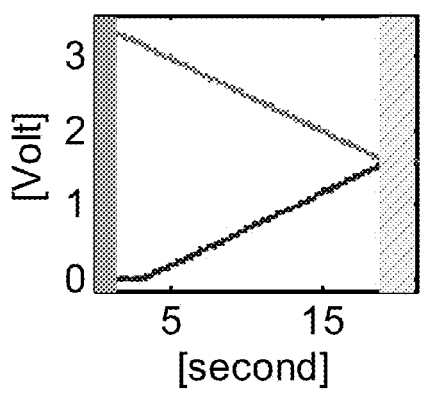
FIG. 13B

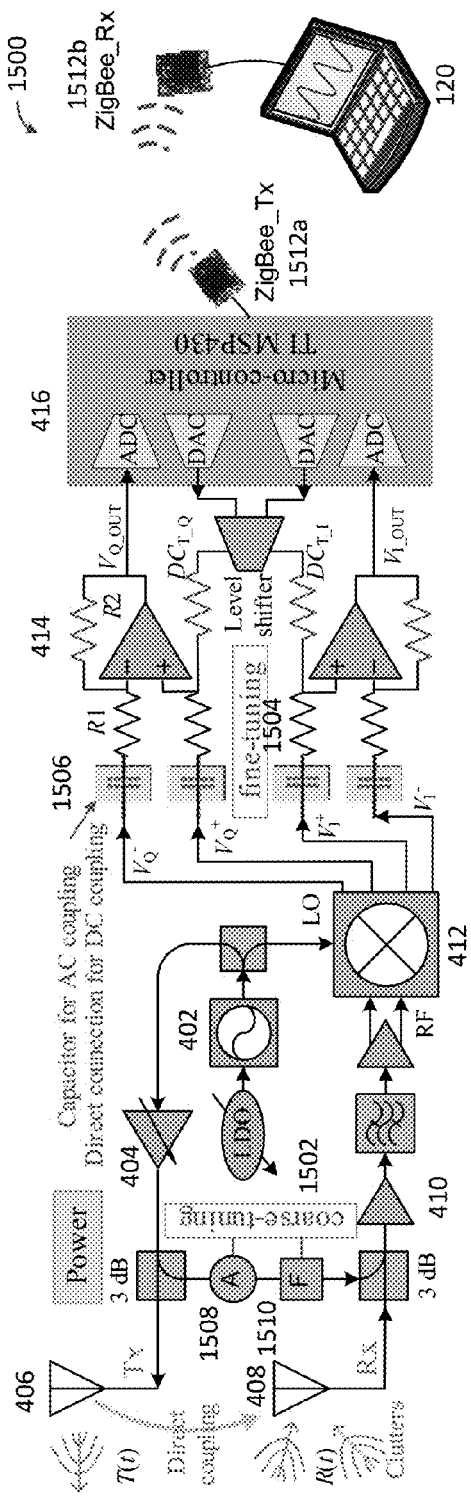
FIG. 15
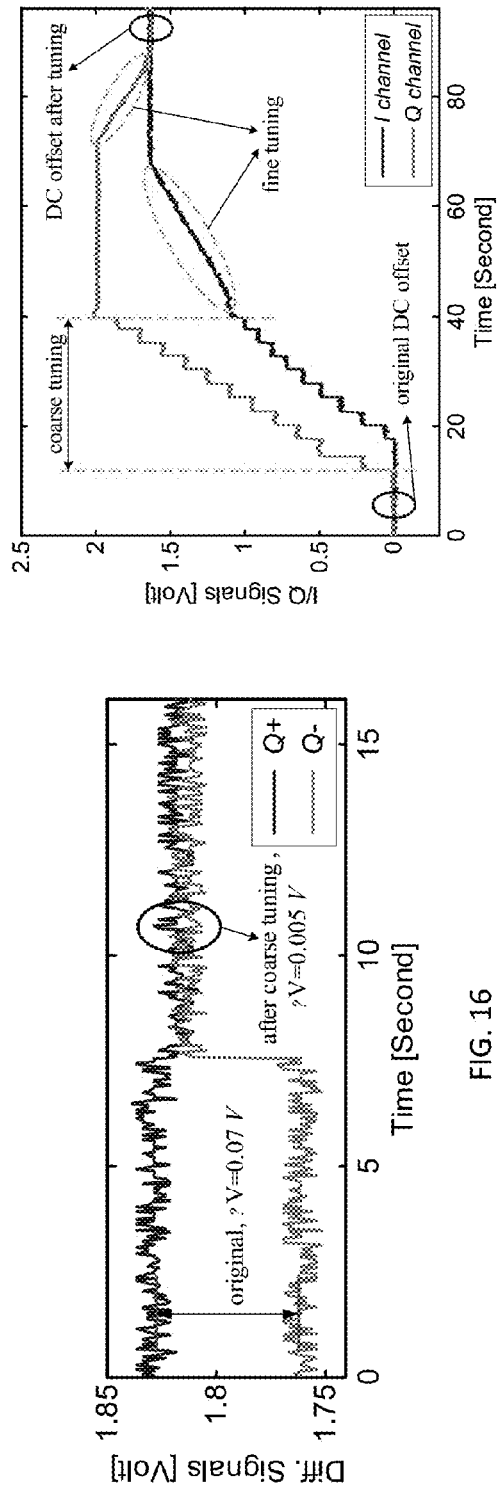
FIG. 17
FIG. 16

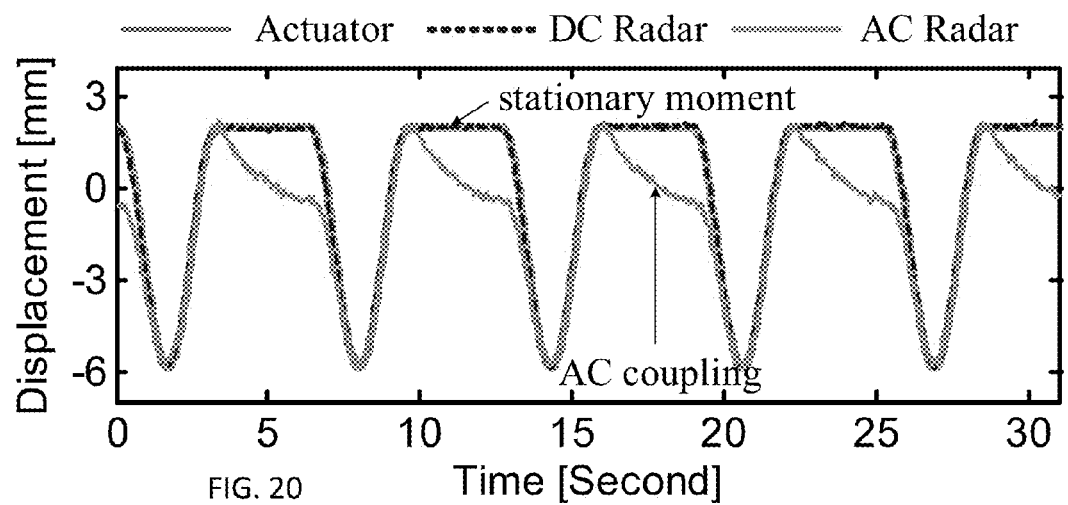
FIG. 20
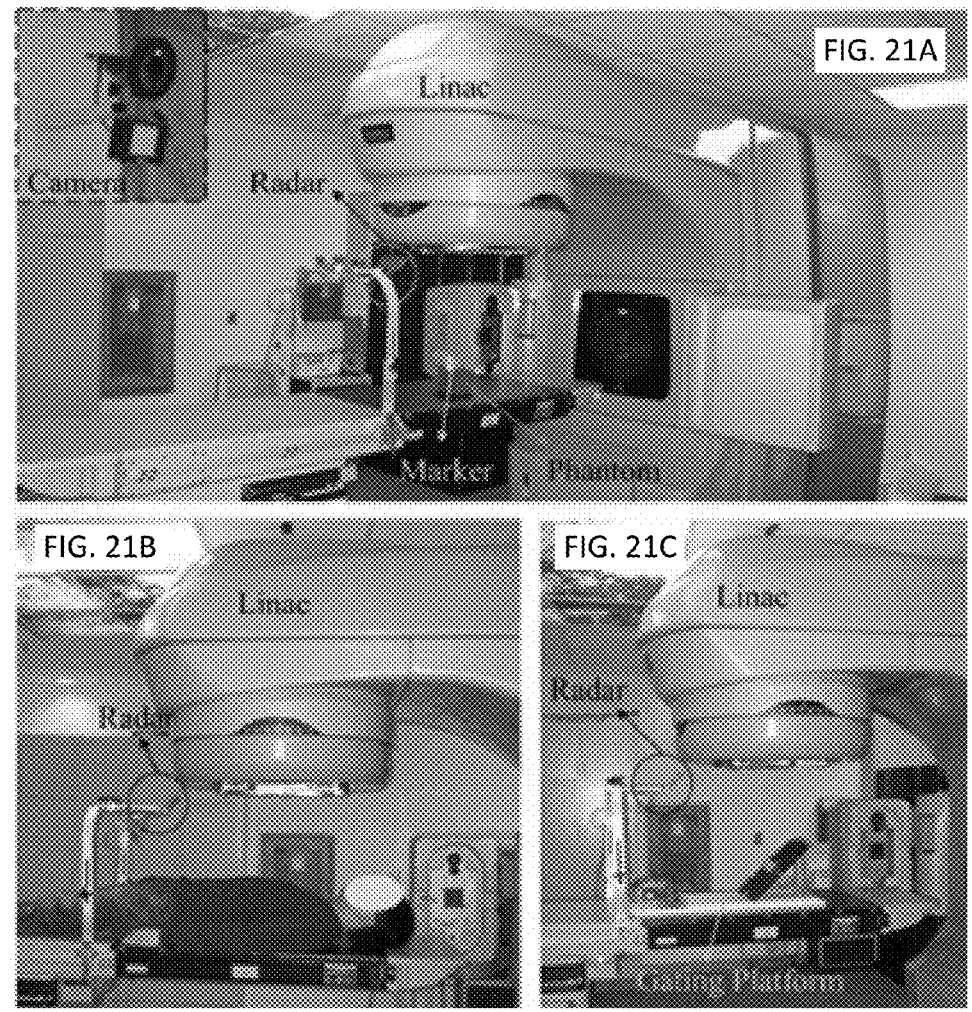

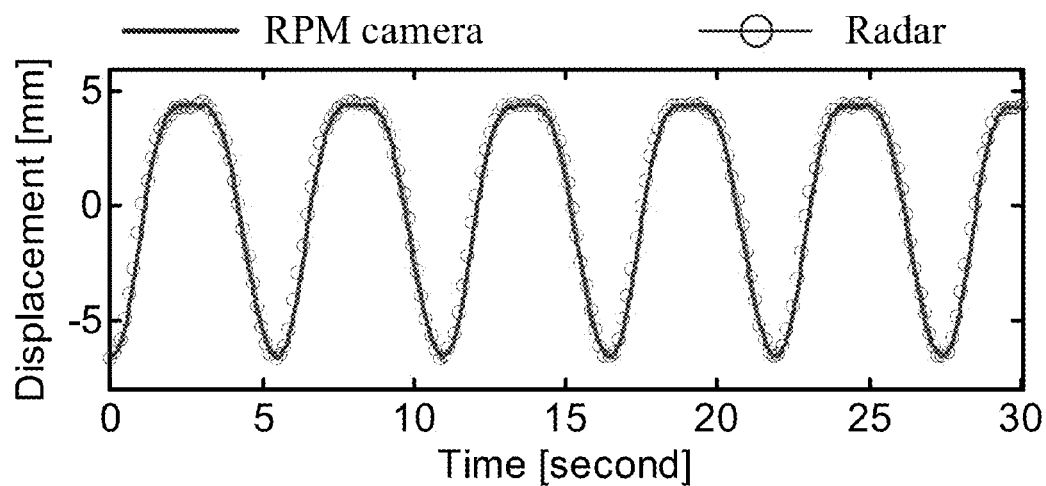
FIG. 22
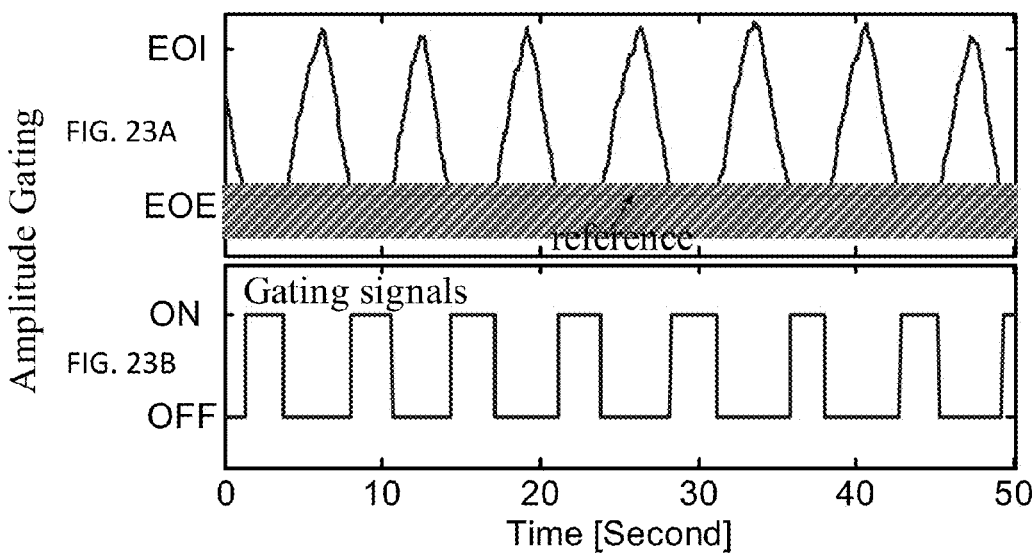
FIG. 23A
FIG. 23B

SYSTEM, METHOD AND APPARATUS FOR TRACKING TARGETS DURING TREATMENT USING A RADAR MOTION SENSOR

CROSS REFERENCE TO RELATED APPLICATIONS

This patent application is a non-provisional patent application of U.S. patent application 61/579,971 filed on Dec. 23, 2011 and entitled "Doppler Radar Measurement for Gated Lung Cancer Radiotherapy," which is hereby incorporated by reference in its entirety.

FIELD OF THE INVENTION

The present invention relates generally to the field of radar-based systems and, more particularly, to a system, method and apparatus for tracking targets during treatment using a radar motion sensor.

STATEMENT OF FEDERALLY FUNDED RESEARCH

None.

BACKGROUND OF THE INVENTION

Cancer is the second leading cause of deaths in the US. According to the American Cancer Society, 1.6 million new cancer cases will be diagnosed and about 600,000 people will die from the disease in 2012. Radiation therapy is a major modality for treating cancer patients. Moreover, lung cancer is the leading cause of cancer death in the United States among every ethnic group. It accounts for about 12% of all newly diagnosed cancers, and about 29% of all cancer deaths. Every day, approximately 439 Americans die from lung cancer. In fact, more people die from lung cancer each year than breast, prostate, colon, liver, kidney and melanoma cancers combined. The treatment outcome of the current modalities has been poor; the 5-year overall survival rate for lung cancer is about 15%.

Studies have shown that an increased radiation dose to the tumor will lead to improved local control and survival rates. However, in many anatomic sites (e.g., lung and liver), the tumors can move significantly (~2-3 cm) with respiration. The respiratory tumor motion has been a major challenge in radiotherapy to deliver sufficient radiation dose without causing secondary cancer or severe radiation damage to the surrounding healthy tissue [27, 28].

Motion-adaptive radiotherapy explicitly accounts for and tackles the issue of tumor motion during radiation dose delivery, in which respiratory-gating and tumor tracking are two promising approaches. Respiratory gating limits radiation exposure to a portion of the breathing cycle when the tumor is in a predefined gating window [29]. Tumor tracking, on the other hand, allows continuous radiation dose delivery by dynamically adjusting the radiation beam so that it follows the real-time tumor movement. For either technique to be effective, accurate measurement of the respiration signal is required. Conventional methods for respiration measurement are undesirable because they are either invasive to the patient or do not have sufficient accuracy.

For instance, measurement based on fiducial markers requires an invasive implantation procedure and involves serious risks to the patient, e.g., pneumothorax for lung cancer patients [30]. These can be either radiopaque metal markers tracked fluoroscopically [2]-[4] or small wireless transponders tracked using non-ionizing electromagnetic fields [5]. While the accuracy of marker tracking is clinically sufficient (~2 mm) [6], the implantation procedure is invasive and may cause various side effects such as pneumothorax, bleeding/lung collapse, infections, respiratory failure requiring ventilator support, vasovagal reaction causing cardiac arrhythmias and even death in rare circumstance [7, 8]. These risks have greatly limited the acceptance of marker based tracking in lung cancer radiotherapy.

In markerless tracking, lung tumors are tracked in fluoroscopy without implanted fiducial markers based on computer vision [9, 10, 11] or machine learning techniques [12]. A major drawback with these techniques is that they require separate fluoroscopic images be acquired and analyzed by clinicians prior to each treatment fraction, which makes it difficult to be implemented in clinical routine. Another issue with tumor tracking using fluoroscopy is the imaging dose. The main risk for prolonged thoracic fluoroscopy is skin burns [13]. The entrance skin dose rate is about 10 mGy/min for typical fluoroscopic parameters used for thoracic imaging, which amounts to 300 mGy for 30 min beam on time. Beside issues like skin burns, the additional imaging dose may also induce secondary cancer or genetic defects [14].

An alternative to localizing tumors directly in fluoroscopy is through external respiratory surrogates, such as patient surface or tidal volume [15]. Kubo et al. developed a respiratory monitoring system that tracks infrared reflective markers placed on the patient's abdomen surface using a video camera [16]. Another commonly used device to monitor respiration is the spirometer [17], which measures the time-integrated air flow and provides the lung volume information from a baseline (e.g., end of exhale). Siemens Medical Systems has a monitoring interface that receives the respiratory signal from a pressure cell on a belt around the patient that senses pressure changes as the patient breathes. All these respiratory monitoring devices give a 1-dimensional output, and effectively measure the breathing signal from a single point. They do not provide any information beyond the point of measurement. For some complicated breathing patterns, this information may not be sufficient to derive the tumor location accurately. More recently, 3D surface imaging systems using video cameras are able to obtain surface images and monitor the patient's surface in real time [18]. Although this technique is noncontact, the reconstructed surface images are sensitive to ambient lighting as well as the clothing around the patient, which can be problematic for the purpose of tumor tracking.

The measurement of external respiration surrogates using infrared reflective marker, spirometer, or pressure belt etc., generally lacks sufficient accuracy to infer the internal tumor position, because they only provide a point measurement or a numerical index of the respiration [31]. In addition, these devices have to be in close contact with the patient in order to function. This often brings discomfort to the patient and can lead to additional patient motion during dose delivery. To that end, accurate respiration measurement which does not require invasive procedures or patient contact is urgently needed in order to realize the potential of motion-adaptive radiotherapy.

Continuous-wave (CW) radar sensor provides a non-contact and non-invasive approach for respiration measurement [19, 20, 21, 32, 33]. Instead of measuring the marker, it directly measures the periodic motion of the body (e.g., breathing and heartbeat), which has better correlation with the lung tumor motion. Moreover, the radar system is insensitive to clothing and chest hair, due to microwave penetration, making it better than the existing contact devices that are sensitive to the surrounding environment. For example, a quadrature Doppler radar has been described in [42]. A fast solution to build a vital sign radar in ordinary laboratories was presented in [22]. Although many results were demonstrated using bench-top prototypes or board-level integration, the potential of being integrated on a small semiconductor chip was also demonstrated [23].

In radar respiration measurement, the radar sensor suffers from DC offset at the RF front-end output, which is mainly caused by the reflections from stationary objects surrounding the body. The DC offset may saturate or limit the dynamic range of the following stages of baseband amplifiers. To overcome this demerit, AC coupling has been commonly used in radar sensors. However, due to the high-pass characteristics of the coupling capacitor, AC coupling leads to significant signal distortion when the target motion has a very low frequency or a DC component. Respiration is such a motion that is low frequency of less than 0.5 Hz, and tends to rest for a while at the end of expiration, i.e., there is a short stationary moment after lung deflation. This is a problem in radar respiration measurement. To deal with it, several approaches, such as high RF-LO isolation mixers [34], have been introduced to employ DC coupling in radar sensors. However, these approaches are either cumbersome to implement or do not completely remove DC offsets and limit the dynamic range of the baseband amplifiers.

SUMMARY OF THE INVENTION

Accurate respiration measurement is crucial in motion-adaptive cancer radiotherapy. Conventional methods for respiration measurement are undesirable because they are either invasive to the patient or do not have sufficient accuracy. In addition, measurement of external respiration signal based on conventional approaches requires close patient contact to the physical device which often causes patient discomfort and undesirable motion during radiation dose delivery. The present invention provides a continuous-wave (CW) radar sensor to provide a non-contact and non-invasive approach for respiration measurement. One embodiment of the radar sensor was designed with DC coupled adaptive tuning architectures that include RF coarse-tuning and baseband fine-tuning, which allows the radar sensor to precisely measure movement with stationary moment and always work with the maximum dynamic range. The accuracy of respiration measurement with the radar sensor in accordance with one embodiment of the present invention was experimentally evaluated using a physical phantom, human subject and moving plate in a radiotherapy environment. It was shown that respiration measurement with radar sensor while the radiation beam is on is feasible and the measurement has a sub-mm accuracy when compared with a commercial respiration monitoring system which requires patient contact. The radar sensor in accordance with the present invention provides accurate, non-invasive, and non-contact respiration measurement and therefore has a great potential in motion-adaptive radiotherapy.

The present invention provides a method for controlling a treatment device in accordance with one embodiment by generating a microwave signal, radiating the microwave signal to a subject, and receiving a modulated microwave signal from the subject. The modulated microwave signal is processed to provide a subject motion information using a sensor having an arctangent-demodulation microwave interferometry mode. A location of a target on or within the subject is determined based on the subject motion information and a three-dimensional model for the subject and the target. One or more control signals are generated based on the location of the target, and the treatment device is controlled using the one or more control signals to treat the target on or within the subject. This method can be implemented as a computer program embedded in a computer readable medium in which the process steps are performed by one or more code segments.

In addition, the present invention provides a radar sensor that includes a microwave signal source, a first amplifier connected to the microwave signal source, and one or more transmitting antennas connected to the first amplifier. The radar sensor also includes one or more receiver antennas, a second amplifier connected to the one or more receiver antennas, a signal mixer connected to the microwave signal source and the second amplifier, a baseband amplifier connected to the signal mixer, and one or more processors connected to the baseband amplifier. The one or more processors provide an arctangent-demodulation microwave interferometry mode and a subject motion information. In another embodiment, the radar sensor includes radio frequency course-tuning circuit and/or a baseband fine-tuning circuit.

Moreover, the present invention provides a treatment system that includes a treatment device, a controller and a radar sensor. The radar sensor includes a microwave signal source, a first amplifier connected to the microwave signal source, and one or more transmitting antennas connected to the first amplifier. The radar sensor also includes one or more receiver antennas, a second amplifier connected to the one or more receiver antennas, a signal mixer connected to the microwave signal source and the second amplifier, a baseband amplifier connected to the signal mixer, and one or more processors connected to the baseband amplifier. The one or more processors provide an arctangent-demodulation microwave interferometry mode and a subject motion information. The controller is communicably connected to the treatment device and the one or more processors of the radar sensor. The controller determines a location of a target on or within a subject based on the subject motion information and a three-dimensional model for the subject and the target, generates one or more control signals based on the location of the target, and controls the treatment device using the one or more control signals to treat the target on or within the subject. The one or more control signals can start and stop a beam of the treatment device or steer the beam of the treatment device. In another embodiment, the radar sensor includes radio frequency course-tuning circuit and/or a baseband fine-tuning circuit.

The present invention is described in detail below with reference to the accompanying drawings.

BRIEF DESCRIPTION OF THE DRAWINGS

The above and further advantages of the invention may be better understood by referring to the following description in conjunction with the accompanying drawings, in which:

FIG. 1 shows a motion-adaptive treatment system based on radar respiration sensing in accordance with one embodiment of the present invention;

FIGS. 2A and 2B show examples of a respiratory-gated treatment mechanism (FIG. 2A), and a target tracking treatment mechanism (FIG. 2B) in accordance with the present invention;

FIG. 12 is a block diagram of an experimental setup a radar sensor in accordance with another embodiment of the present invention FIG. 1;

FIGS. 13A-13C are graphs showing the DC tuning process and radar measurement result with and without DC tuning using the circuit shown in FIG. 12;

FIG. 15 is a block diagram of the DC coupled radar sensor system 1500 with RF coarse-tuning and baseband fine-tuning architectures in accordance with yet another embodiment of the present invention;

FIG. 16 is a graph showing the DC offset difference of the differential Q channel before and after the coarse-tuning using the circuit shown in FIG. 15;

FIG. 17 is a graph showing the DC offsets of the circuit shown in FIG. 15 were adaptively tuned to the desired level by the process of coarse tuning and fine tuning;

FIG. 20 is a graph showing the programmed actuator movement compared with the movements measured by AC coupled radar and DC coupled radar in an electronic lab using the circuit shown in FIG. 15;

FIGS. 21A-21C show experimental setups in accordance with the present invention;

FIG. 22 is a graph showing phantom motion measured by radar with the LINAC radiation beam turned on, compared with the same phantom motion measured by Varian's RPM system;

FIGS. 23A and 23B are graphs showing radar measured respiration signal (FIG. 23A), and the generated gating signal (FIG. 23B)

DETAILED DESCRIPTION OF THE INVENTION

Figure 3:
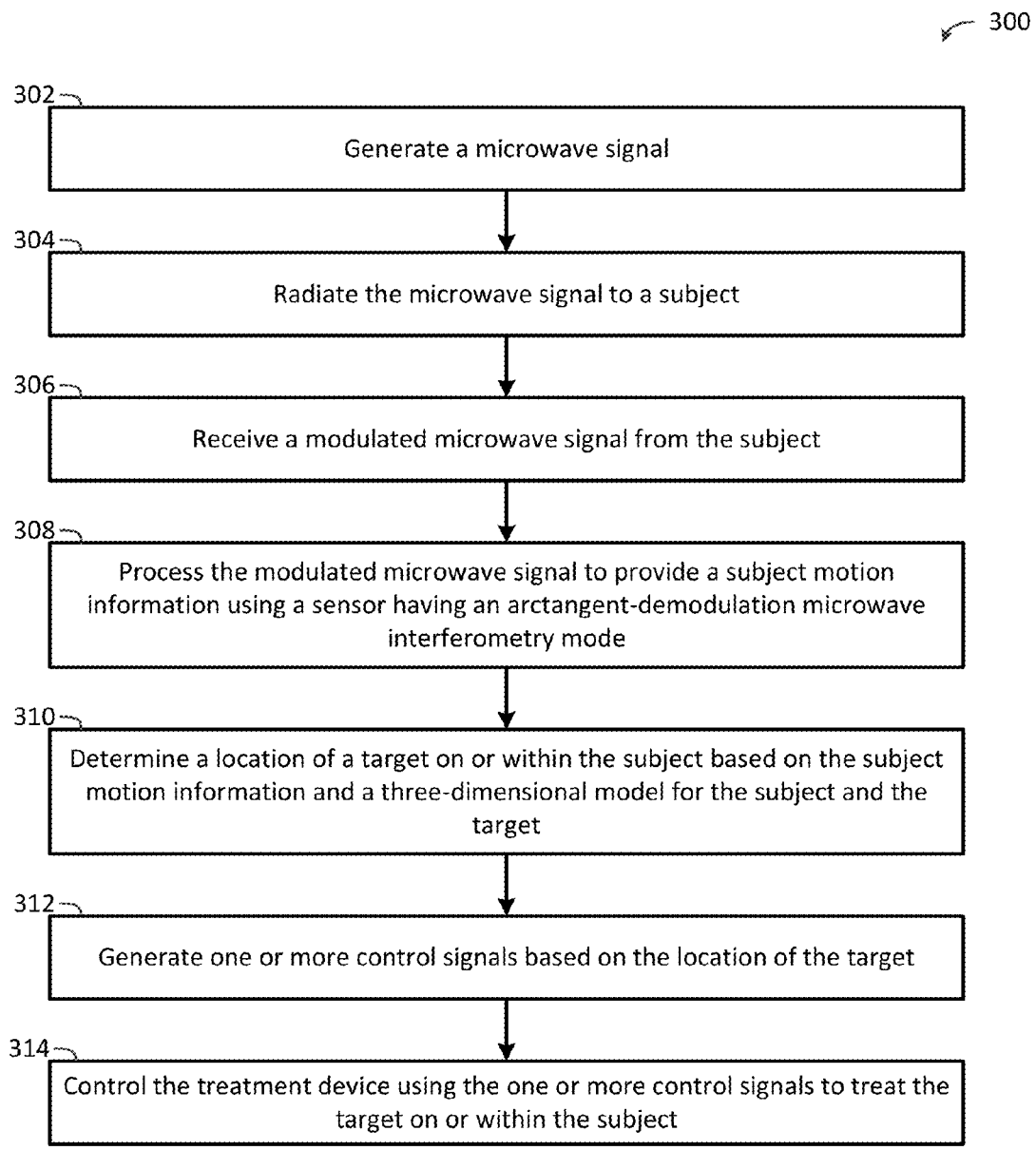
FIG. 3 is a flow chart depicting a method for controlling a treatment device in accordance with one embodiment of the present invention.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention. The discussion herein relates primarily to accurate respiration measurement using radar sensors for motion-adaptive cancer radiotherapy, but it will be understood that the concepts of the present invention are applicable to any radar sensor.

The motion-adaptive treatment system based on radar respiration sensing in accordance with one embodiment of the present invention is shown in FIG. 1. The treatment process 100 includes two basic stages: (1) treatment preparation 102, which consists of subject simulation and treatment planning; and (2) treatment execution 104, which delivers a dose to the subject 106 using a beam 108 from a treatment device 110. The subject 106 can be a human or animal. The treatment device 110 can be a radiation beam device, a laser or other suitable treatment device. The beam 108 can be an electron beam, a gamma beam, a photon beam, a proton beam, a X-ray beam or other suitable beam. The treatment process 100 can be broken down into four steps: (Step I) scanning; (Step II) radar sensing during treatment; (Step III) target tracking algorithm; and (Step IV) beam control.

In the first step, subject simulation includes collecting subject and target geometrical information 112 by scanning the subject 106 and target 114 using a scanning device and generating a three-dimensional model for the subject 106 and target 114 based on the subject and target geometrical information 112 [27, 28]. The scanning device can be a computed tomography (CT) device, a magnetic resonance imaging (MRI) device, a magnetic resonance tomography (MRT) device, a positron emission tomography (PET) device, a single photon emission computed tomography (SPECT) device, an ultrasound device, or other suitable scanning device. The target 114 can be a tumor, a growth, a tissue, a skin cancer or other treatment area on or within the subject 106. The subject's breathing pattern is also examined at this stage. Those subjects 106 who cannot exhibit stable breathing patterns would be most likely excluded from the motion-adaptive treatment. Treatment planning is a virtual process that designs the subject treatment using the subject model built at the simulation stage.

In the second step, the treatment device 110, such as a medical linear accelerator (LINAC), works together with two radar sensors, shown as inset (a), that dynamically monitor the chest wall and the abdomen to provide the real-time motion information 116. The treatment device 110 could also be integrated with a radar sensor having beam-scanning capability, shown as inset (b), which makes it possible to use one radar sensor to simultaneously measure the breathing motions at multiple body locations [39].

In the third step, the target tracking algorithm combines the real-time motion information 116 (e.g., chest wall and abdomen motion information) together with the pre-collected subject model to extract the target locations 118 in real-time. Then a controller 120 utilizes the extracted target location information 118 to control the treatment device 110 to either perform gated beam therapy or steer the beam to track the target 114. The inset (c) shows one embodiment of a radar sensor 122 in accordance with the present invention that provides a 2.4 GHz miniature radar sensor with the size of 5 cm by 5 cm. The radar sensor 122 was configured with a ZigBee module for wireless data transmission, which allows wireless monitoring of the respiration outside the treatment room and eliminates a bunch of cables that may constrain the radar installation to the treatment device 110. The radar sensor 112 works in an arctangent-demodulated microwave interferometry mode to achieve a sub-millimeter motion sensing accuracy [40].

In the radar treatment system, the subject 106 lies on the treatment couch 124 under the radar sensor 122 and breathes normally. The radar sensor 122 measures the breathing signal and wirelessly transmits it to a controller 120 (e.g., a laptop with a LabView signal processing interface running in real time). The patient can be coached to breathe to maintain a relatively regular breathing pattern by looking at the real-time visual feedback from the screen of the controller 120 or following some kind of audio guidance [28].

In respiratory-gated treatment, the mechanism of which is shown in FIG. 2A, the treatment dose is delivered to the target 114 (e.g., tumor) only when it moves into the beam coverage. When the target moves out of the beam coverage, the beam 108 is turned off 200. Gating of the beam 108 can be based on either amplitude or phase of the respiration signal 204. Duty cycle and residual motion are two important parameters, which characterize a gated treatment. Duty cycle is the percentage of time that beam 108 is turned on during a breathing cycle. Residual motion is the amount of target motion during beam on 206. In respiratory gating, there is a tradeoff between duty cycle and residual motion. A longer duty cycle means longer beam exposure to the target 114 and shorter overall treatment time, but it also means larger residual motion of the target 114, which will expose more healthy tissues to the beam 108. The duty cycle is determined by the doctor at the treatment preparation stage 102, according to specific subjects and different treatment strategies. Respiratory gating has to leverage the tradeoff between duty cycle and residual target motion. However, this demerit is eliminated in the target tracking type of treatment, in which, the beam 108 is always on and dynamically follows the moving target 114 in real time, as shown in FIG. 2B. This is technologically more challenging than respiratory gating treatments. For radiotherapy treatments based on LINACs, tumor tracking can be implemented by tracking the tumor motion using a dynamic multi-leaf collimator (MLC) that shapes the radiation beam [29]. In order for the radiation beam 108 to dynamically follow the tumor 114, the location of the tumor 114 must be known with high accuracy and in real time.

Now referring to FIG. 3, a method 300 for controlling a treatment device 110 in accordance with one embodiment of the present invention is shown. A microwave signal is generated in block 302, the microwave signal is radiated to a subject (e.g., human, animal, etc.) in block 304, and a modulated microwave signal is received from the subject in block 306. The modulated microwave signal is processed to provide a subject motion information (e.g., a chest wall motion information and an abdomen motion information, etc.) using a sensor having an arctangent-demodulation microwave interferometry mode in block 308. A location of a target (e.g., tumor, growth, tissue, skin cancer, etc.) on or within the subject is determined based on the subject motion information and a three-dimensional model for the subject and the target in block 310. One or more control signals are generated based on the location of the target in block 312, and the treatment device (e.g., radiation beam device, laser, etc.) is controlled using the one or more control signals to treat the target on or within the subject in block 314. The one or more control signals can start and stop a beam (e.g., electron, gamma, photon, proton, X-ray, etc.) of the treatment device or steer the beam of the treatment device. This method can be implemented as a computer program embedded in a computer readable medium in which the process steps are performed by one or more code segments.

The subject motion information and the three-dimensional model for the subject and the target can be used to determine an exact location of the target on or within the subject. Moreover, all the steps can be performed in real-time. The three-dimensional model can be generated based on a subject and target geometrical information that is obtained by scanning the subject and the target using a scanning device (e.g., CT, MRI, MRT, PET, SPECT, ultrasound, etc.). The three-dimensional model may also include one or more organs or body parts. A treatment plan for the subject can be designed using the three-dimensional model.

Figure 4:
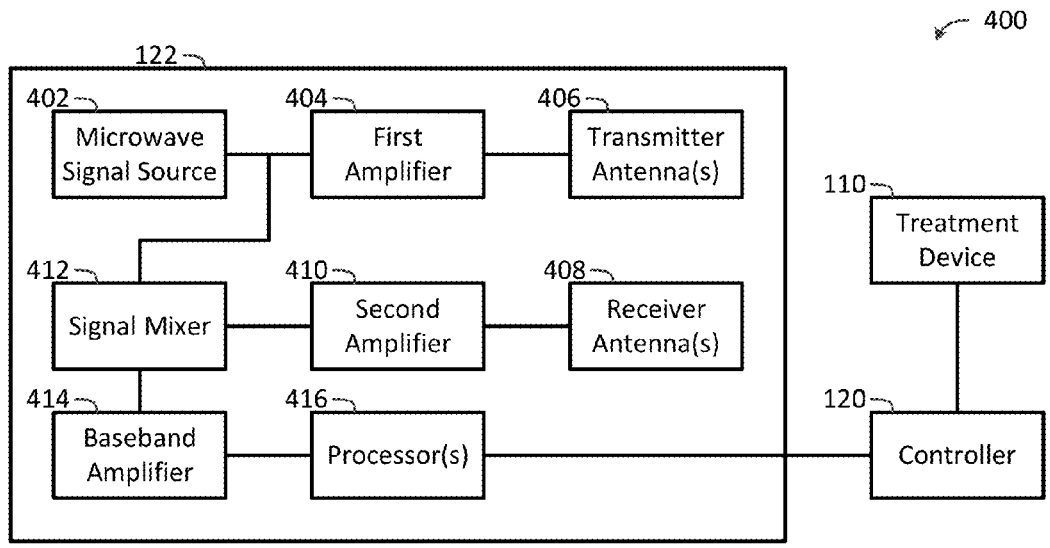
FIG. 4 is a block diagram of a treatment system in accordance with another embodiment of the present invention.

Referring now to FIG. 4, a block diagram of treatment system 400 in accordance with one embodiment of the present invention is shown. The system 400 includes a treatment device 110 (e.g., radiation beam device, laser, etc.), a controller 120 and a radar sensor 122. The radar sensor 122 includes a microwave signal source 402, a first amplifier 404 (e.g., fixed or variable) connected to the microwave signal source 402, and one or more transmitting antennas 406 (e.g., fixed or variable) connected to the first amplifier 404. The radar sensor 122 also includes one or more receiver antennas 408, a second amplifier 410 connected to the one or more receiver antennas 408, a signal mixer 412 connected to the microwave signal source 402 and the second amplifier 410, a baseband amplifier 414 (e.g., AC coupled or DC coupled) connected to the signal mixer 412, and one or more processors connected to the baseband amplifier 414. The one or more processors 416 provide an arctangent-demodulation microwave interferometry mode and a subject motion information (e.g., a chest wall motion information and an abdomen motion information, etc.). The controller 120 is communicably connected to the treatment device 110 and the one or more processors 416 of the radar sensor 122. The controller 120 determines a location of a target (e.g., tumor, growth, tissue, skin cancer, etc.) on or within a subject (e.g., human, animal, etc.) based on the subject motion information and a three-dimensional model for the subject and the target, generates one or more control signals based on the location of the target, and controls the treatment device 110 using the one or more control signals to treat the target on or within the subject. The one or more control signals can start and stop a beam (e.g., electron, gamma, photon, proton, X-ray, etc.) of the treatment device 110 or steer the beam of the treatment device 110. The one or more processors 416 may further provide a DC offset calibration.

The subject motion information and the three-dimensional model for the subject and the target can be used to determine an exact location of the target on or within the subject. Moreover, all the steps can be performed in real-time. The three-dimensional model can be generated based on a subject and target geometrical information that is obtained by scanning the subject and the target using a scanning device (e.g., CT, MRI, MRT, PET, SPECT, ultrasound, etc.). The three-dimensional model may also include one or more organs or body parts. A treatment plan for the subject can be designed using the three-dimensional model.

Figure 5:
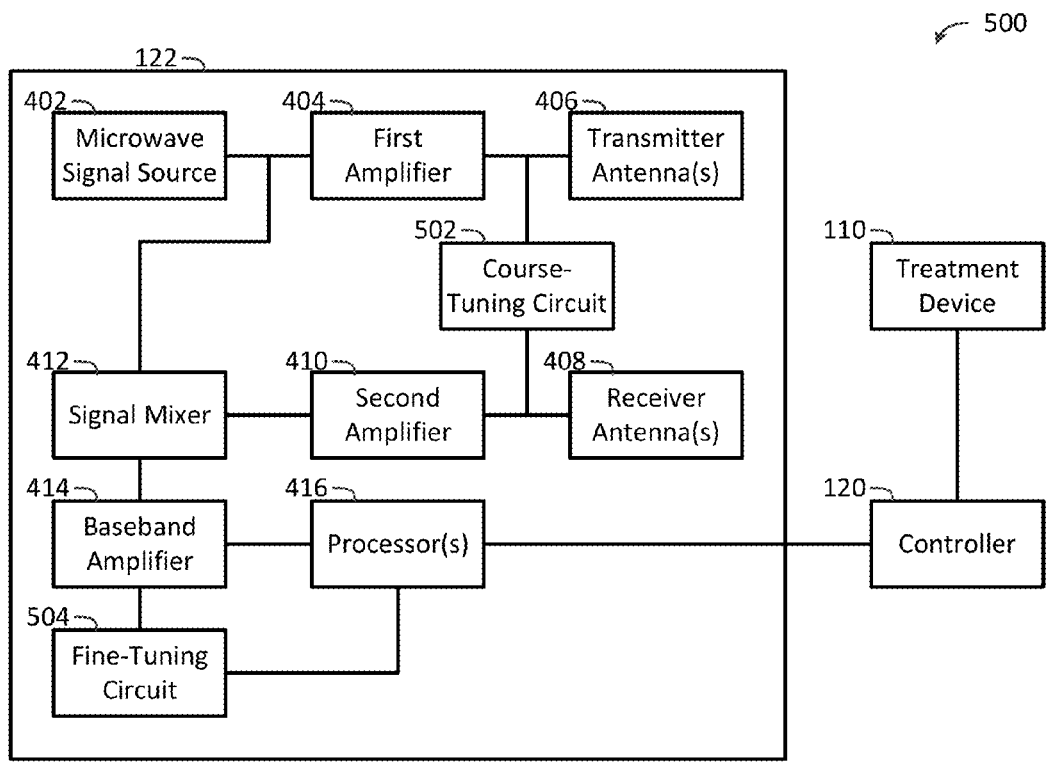
FIG. 5 is a block diagram of a treatment system in accordance with yet another embodiment of the present invention.

Now referring to FIG. 5, a block diagram of treatment system 500 in accordance with one embodiment of the present invention is shown. The system 500 includes a treatment device 110 (e.g., radiation beam device, laser, etc.), a controller 120 and a radar sensor 122. The radar sensor 122 includes a microwave signal source 402, a first amplifier 404 (e.g., fixed or variable) connected to the microwave signal source 402, and one or more transmitting antennas 406 (e.g., fixed or variable) connected to the first amplifier 404. The radar sensor 122 also includes one or more receiver antennas 408, a second amplifier 410 connected to the one or more receiver antennas 408, a signal mixer 412 connected to the microwave signal source 402 and the second amplifier 410, a baseband amplifier 414 (e.g., AC coupled or DC coupled) connected to the signal mixer 412, and one or more processors connected to the baseband amplifier 414. A radio frequency course-tuning circuit 502 is connected to the one or more transmitter antennas 406, the one or more receiver antennas 408 and the one or more processors 416. A baseband fine-tuning circuit 504 is connected to the baseband amplifier 414 and the one or more processors 416. The one or more processors 416 provide an arctangent-demodulation microwave interferometry mode and a subject motion information (e.g., a chest wall motion information and an abdomen motion information, etc.). The controller 120 is communicably connected to the treatment device 110 and the one or more processors 416 of the radar sensor 122. The controller 120 determines a location of a target (e.g., tumor, growth, tissue, skin cancer, etc.) on or within a subject (e.g., human, animal, etc.) based on the subject motion information and a three-dimensional model for the subject and the target, generates one or more control signals based on the location of the target, and controls the treatment device 110 using the one or more control signals to treat the target on or within the subject. The one or more control signals can start and stop a beam (e.g., electron, gamma, photon, proton, X-ray, etc.) of the treatment device 110 or steer the beam of the treatment device 110. The one or more processors 416 may further provide a DC offset calibration.

The radio frequency course-tuning circuit 502 adaptively pulls up both an I channel and a Q channel to a specified levels. The radio frequency course-tuning circuit 502 may include a first coupler connected between the first amplifier 404 and the one or more transmitter antennas 406, a second coupler connected between the second amplifier 410 and the one or more receiver antennas 408, and a voltage-controlled attenuator and a voltage-controlled phase shifter connected the first coupler and the second coupler. The baseband fine-tuning circuit 504 precisely adjusts both an I channel DC offset and a Q channel DC offset to a specified levels. The baseband fine-tuning circuit 504 includes a level shifter connected to the baseband amplifier 414 and the one or more processors 416. The radar sensor 122 may include one or both of these circuits.

The subject motion information and the three-dimensional model for the subject and the target can be used to determine an exact location of the target on or within the subject. Moreover, all the steps can be performed in real-time. The three-dimensional model can be generated based on a subject and target geometrical information that is obtained by scanning the subject and the target using a scanning device (e.g., CT, MRI, MRT, PET, SPECT, ultrasound, etc.). The three-dimensional model may also include one or more organs or body parts. A treatment plan for the subject can be designed using the three-dimensional model.

The various embodiments of the present invention provide a CW radar sensor 122 to provide a non-contact and non-invasive approach for accurate respiration measurement. In one embodiment, the radar sensor 122 uses DC coupled adaptive tuning architectures that include RF coarse-tuning and baseband fine-tuning. The RF tuning was implemented using a path of an attenuator and a phase shifter at the RF front end of the radar sensor 122 [35, 36]. It adds a portion of the transmitter signal to the receiver signal to cancel out most of the DC offset. To further calibrate the remaining DC offset, the baseband fine-tuning architecture was used to adaptively adjust the amplifier bias to the desired level that allows both high gain amplification and maximum dynamic range at the baseband stage. With the above-mentioned DC tuning architectures, the radar sensor 122 is able to precisely measure the low frequency respiration motions with stationary moment. The radar sensor 122 in accordance with one embodiment of the present invention was tested in the lab environment to demonstrate its ability of accurate displacement measurement that preserves DC information of stationary moment. Moreover, the radar sensor 122 was integrated and tested with a linear accelerator (LINAC) to validate its clinical use. In order to achieve accurate radiation beam targeting using respiration measurement, a correlation model was built and validated between the internal tumor target and external respiration signal. This can be decoupled and is generally treated as a separate issue from respiration measurement. In fact, various approaches have been explored to infer the internal target position from external measurement [37, 38]. Therefore, the present invention provides an accurate measurement of respiration in a non-invasive and non-contact way.

Three embodiments of the present invention will now be described. The first embodiment is a 5.8 GHz radar physiological motion sensing system. The second embodiment is a 2.4 GHz DC-coupled radar sensor system with baseband fine-tuning architecture. The third embodiment is a 2.4 GHz DC-coupled radar sensor system with RF course-tuning and baseband fine-tuning architectures. The present invention is not limited to these embodiments or frequencies.

Referring now back to FIG. 1, the radar-based tumor tracking method extracts information about the motion characteristics of the entire thorax (including the tumor 114) from a 4DCT scan. The 4DCT data set is obtained during the 'patient simulation' process, which occurs prior to the first radiotherapy treatment. In the second step, a medical linear accelerator (LINAC) 110 is operated during patient treatment together with a radar physiological sensing system 122 that provides information of the chest wall or/and abdominal movements 116 in real time. The real-time movement information 116 together with the pre-collected image information 112 is processed based on advanced tumor tracking algorithm in the third step. Then the dynamic tumor location information 118 is extracted in real time and used to control the radiation beam 108 of the LINAC 110. In order to achieve high sensing accuracy, sensitivity, and robustness, it is important to combine the high-sensitivity radar with advanced imaging algorithms. Arctangent-demodulated radar interferometry [43] is utilized to realize a sub-millimeter motion sensing accuracy. In order to track the internal lung tumor motion accurately, a physically and physiologically plausible model is constructed for lung motion. The lung motion model takes into consideration the motion characteristics of different organs involved in respiration, including static, rigid and deformable organs. In addition, patient specific tissue properties and relations between external and internal surrogates are obtained from patient volumetric image sets. In the treatment stage of gated radiotherapy, the LINAC 110 delivers radiation dose to the patient 106, based on the geometry data obtained in 4D CT simulation/planning. Doppler radar serves as the patient respiration monitoring system to provide breathing motion outputs used as the reference gating signal. The radar 122 can be placed over the patient's thorax or abdomen, with a distance that can be extended to several meters.

Figure 6:
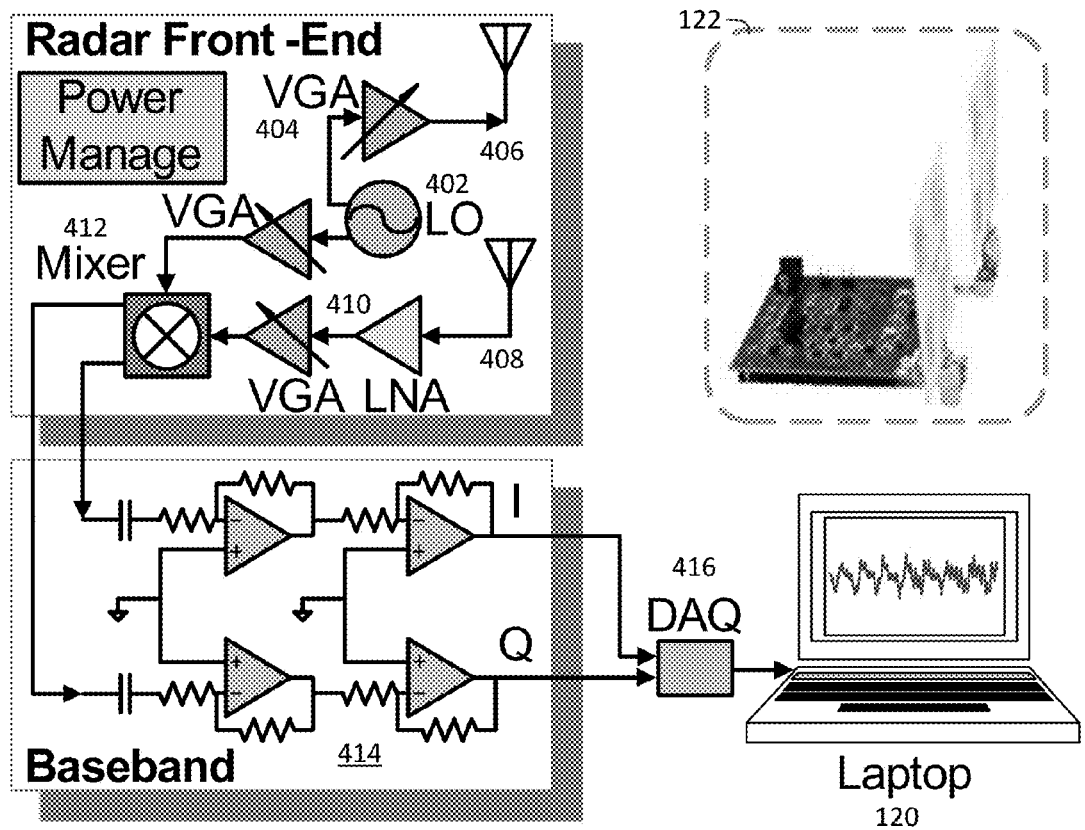
FIG. 6 is a circuit diagram of a 5.8 GHz radar physiological motion sensing system in accordance with one embodiment of the present invention.

Now referring to FIG. 6, a circuit diagram of a 5.8 GHz Doppler radar with quadrature demodulation architecture in accordance with one embodiment of the present invention is shown. The inset of FIG. 6 shows the picture of the radar 122 with a dimension of 75 mm×68 mm. Two patch antennas arrays are used for measurement, with one for transmitting 406 and the other for receiving 408. A single tone microwave signal is radiated toward the patient's chest. The periodic chest motion, caused by breathing, modulates the single tone signal in the phase. The single tone signal including the phase information of the patient's breathing motion is then down-converted to baseband, which is further processed by the two-stage baseband amplifier 414. The amplified baseband signals are sampled by NI USB6009 data acquisition module (DAQ) 416 and then fed into LabVIEW, running on an external computer 120, for real time signal processing. After DC offset calibration and arctangent demodulation, the acquired respiration signals are used to generate the gating signals that control the radiation system 110. The LINAC 110 turns on radiation within the gating window and turns it off outside the window.

The baseband I/Q outputs of the radar are:

$$B(t)_I = A_I \cos[\theta + 4\pi x(t)/\lambda + \Delta\phi(t)] + DC_I \quad (1)$$

$$B(t)_Q = A_Q \sin[\theta + 4\pi x(t)/\lambda + \Delta\phi(t)] + DC_Q \quad (2)$$

where $\theta$ is constant phase offset determined by the initial position of the patient, $x(t)$ is the physiological motion caused by breathing, $\Delta\theta(t)$ is the residual phase noise, $A_I/A_Q$ are the amplitudes and $DC_I/DC_Q$ are the DC offsets of the I/Q channels respectively. After calibration of the DC offsets and I/Q mismatch based on a constellation graph [43], $A_I$ and $A_Q$ will be set to equal and $DC_I$ and $DC_Q$ will be eliminated. The I/Q signals should thus form a portion of the circle. Arctangent demodulation is then applied to accurately demodulate the respiration signal:

$$\psi(t) = \tan^{-1}[B(t)_Q/B(t)_I] + F = \theta + 4\pi x(t)/\lambda + \Delta\phi(t) \quad (3)$$

where F is a multiple of 180° for the purpose of eliminating the discontinuity when $\psi(t)$ crosses the boundary of two adjacent quadrants in the constellation graph. Therefore, actual respiration movement can be derived as $x(t) = x_0 + \phi(t)\lambda/4\pi$, where $x_0$ is a constant depending on the initial position of the target.

Figure 7:
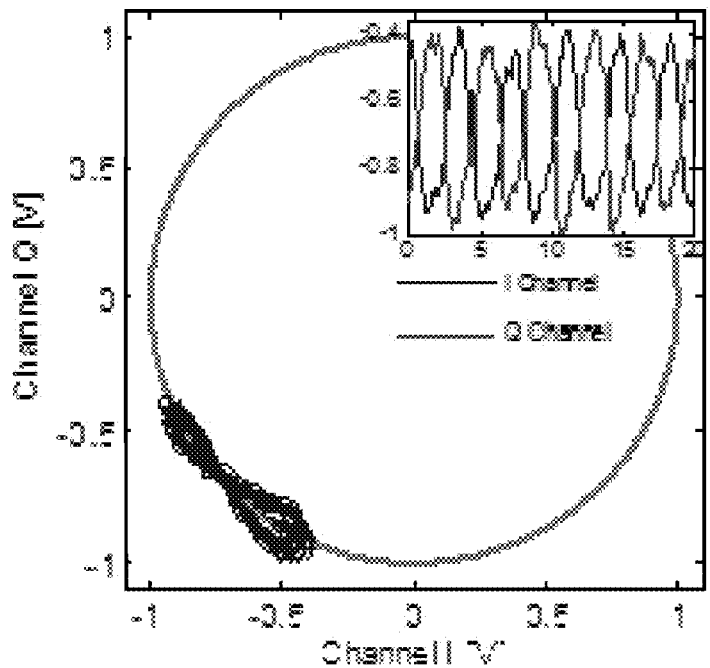
FIG. 7 is a constellation graph of the measured respiration motion using the circuit shown in FIG. 6.

In respiration measurement, a 5.8 GHz radar was used with the subject seating at one meter away from the radar and breathing normally. FIG. 7 shows the measured output signals of the radar I/Q channels after DC and amplitude calibration. The I and Q channel data form a portion of a unit circle. The inset shows the raw data of the I/Q channels.

Different people have different breathing patterns, indicating that the breathing motion not only differs in rhythm but also differs in shapes. Two sets of experiments were carried out to simulate the real clinical environment. In the first experiment, the target person seated in front of the radar at one meter away was asked to breath normally at his own arbitrary rhythm. The Doppler radar recorded the free breathing motions. In the second experiment, the target person was coached to adjust his breathing to maintain a relatively regular respiration by visual feedback from a LabVIEW window.

Figure 8:
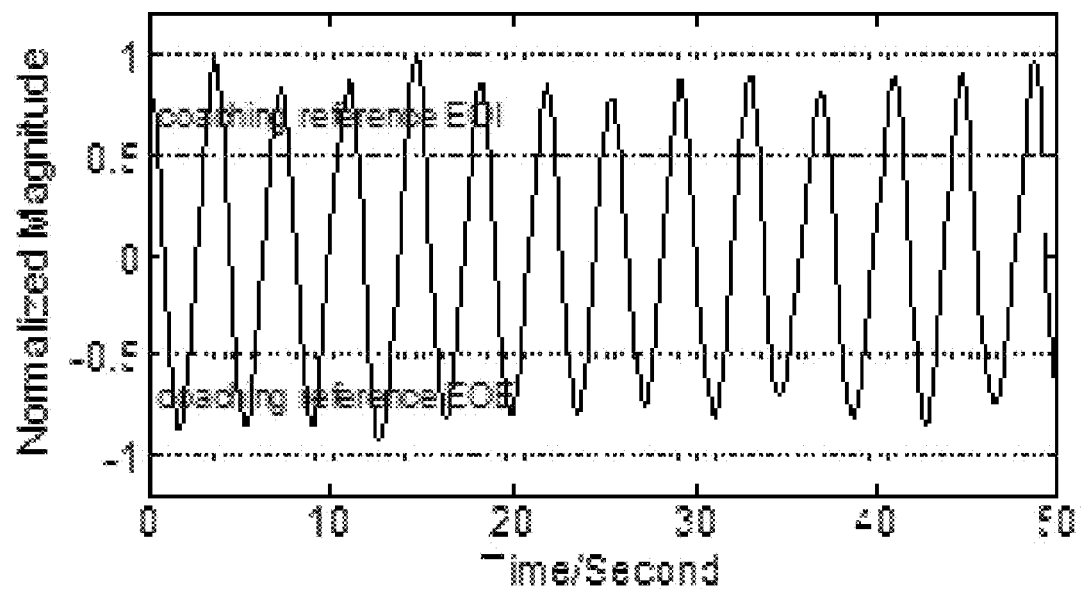
FIG. 8 is a graph of a coached breathing signal with a reproducible pattern using the circuit shown in FIG. 6.
Figure 9:
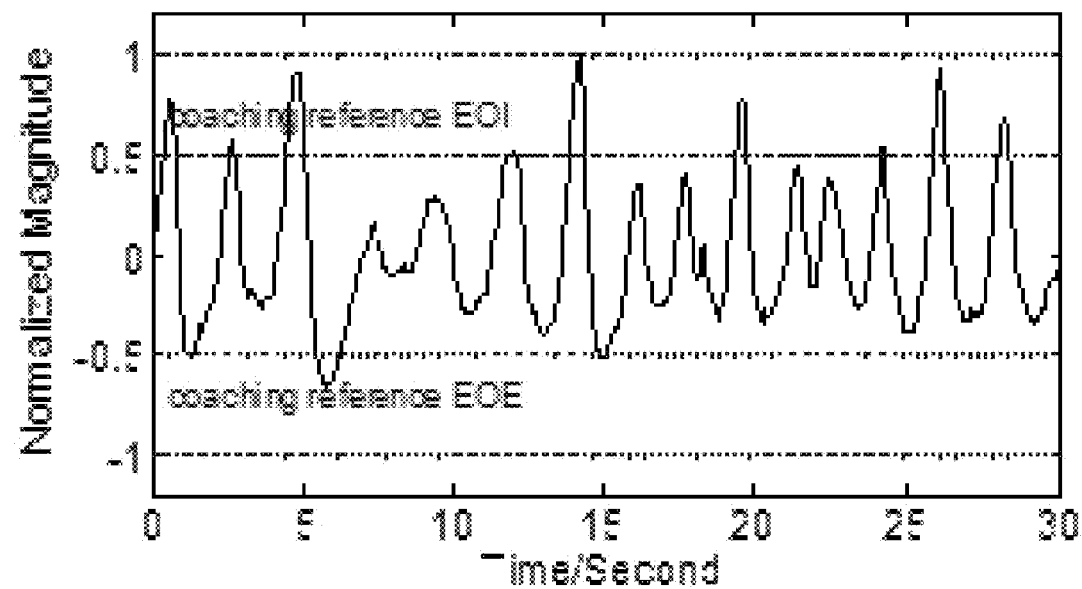
FIG. 9 is a graph of an arbitrary free breathing signal with an irregular pattern using the circuit shown in FIG. 6.

The experiment results are shown in FIG. 8 and FIG. 9. EOI represents end of inspiration and EOE represents end of expiration. Two EOI reference lines were defined on the upper side and two EOE lines were defined on the lower side. The patients were asked to adjust his breathing dynamically to put the EOI/EOE position in between the two reference lines [15]. It is shown in FIG. 9 that without coaching, arbitrary free breathing makes it hard to obtain the gating signal. By looking at the real time signal to dynamically adjust breathing movement, FIG. 8 shows a reproducible respiration motion, from which, gating signal is easy to generate. It should be noted that, with some sort of audio instruction [15], more reproducible respiration signals are expected to be obtained.

Figure 10:
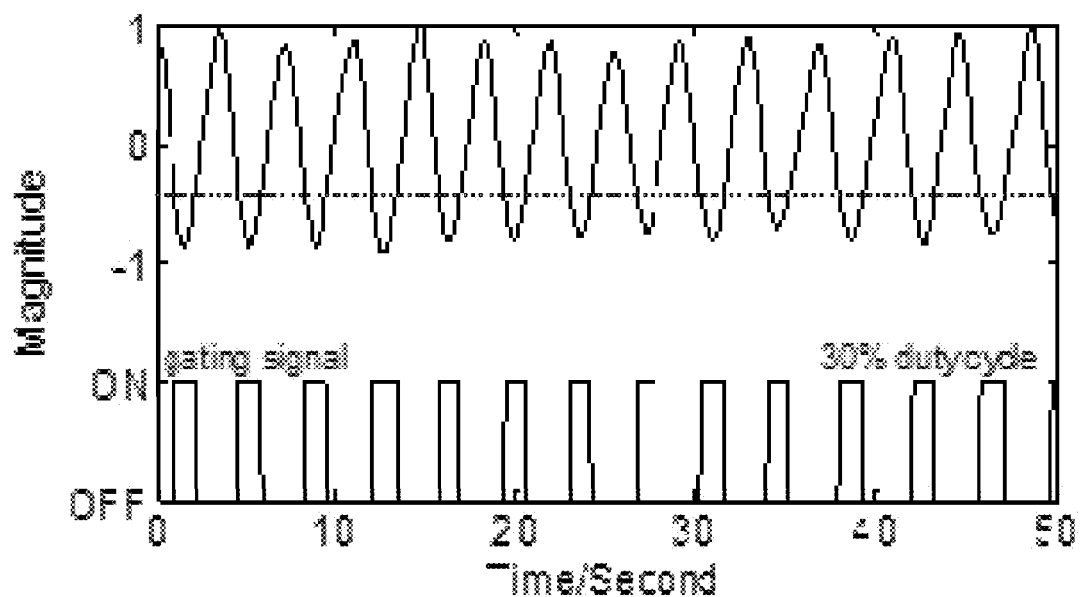
FIG. 10 is a graph of an amplitude gating with a duty cycle of 30% using the circuit shown in FIG. 6.
Figure 11:
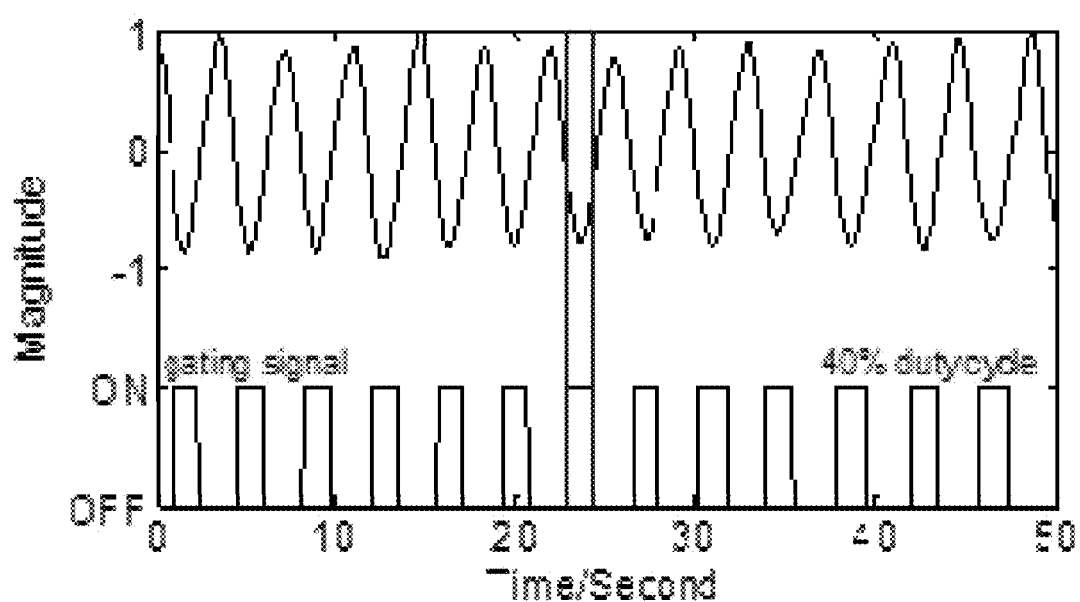
FIG. 11 is a graph of a phase gating with a duty cycle of 40% using the circuit shown in FIG. 6.

The reproducible respiration signals allow both amplitude and phase gating. FIG. 10 shows an example of amplitude gating with a duty cycle of 30% and FIG. 11 shows phase gating with a duty cycle of 40%. The duty cycle is usually 30%-50% for a typical gated radiotherapy treatment. The Doppler radar method accurately measures breathing motions and allows dynamic adjustment of the duty cycles based on amplitude gating or phase gating.

In gated radiotherapy, there are two indices that characterize the goodness of a treatment: duty cycle and residual motion. There is always a tradeoff between these two parameters. A longer duty cycle means higher efficiency and shorter overall treatment time span. On the other hand, it also means larger residual motion, which will expose more healthy tissues to radiation. Therefore, it is necessary to adjust these two parameters to find a good balance for a specific patient. However, this tradeoff is eliminated in a beam tracking type of treatment, where the tumor is dynamically followed by the radiation beam in real time. Of course, this also creates more technological challenges.

In order to accurately track the internal lung tumor motion during respiration, a realistic model for lung motion based on 4DCT is necessary. Respiration is a complex process which results from the action of several muscles. The primary muscles of respiration include the intercostals muscles and the diaphragm. During inhalation, the contraction of both the intercostal muscles and the diaphragm lowers the air pressure in the lungs and causes air to move in. During exhalation, the intercostal muscles and the diaphragm relax and force air out of the lungs. The two actions of the intercostal muscles and diaphragm are related but not identical. They have different effects on internal organ motion in different patients. Therefore, they have to be considered separately and will be controlled by two independent sets of parameters, which will then govern the motion of other organs (lung, liver, etc.).

The organs involved during respiration are divided into three categories with increasing levels of complexity in terms of their motion characteristics: static organs, rigid organs, and deformable organs. In the human thorax, spine can be reasonably assumed to be static. The ribs and the sternum are rigid, and their motion follows the kinematic law. The rib motion is a combination of two movements [24]: a change in the lateral excursion of the ribs and a change in the anteroposterior diameter of the thorax. These two rotations are respectively defined by $\gamma$ and $\lambda$. All other organs are deformable. In general, finite element model (FEM) produces results with greater accuracy for deformable objects. However, because of its high computational nature, it is not suitable for our applications, where real-time performance is required.

The ChainMail algorithm was adapted to model soft tissue deformation as it is efficient and suitable for real-time applications. In the ChainMail algorithm [25], a volumetric object is defined as a set of point elements that are interconnected as links in a chain, allowing each point to move freely without influencing its neighbors, within certain pre-specified limits. When an element of the object reaches this limit, the neighbors are forced to move in a chain reaction that is governed by the stiffness of the links in the mesh. Let $A(x_a, y_a, z_a)$ be the vertex that is being moved and $B(x_b, y_b, z_b)$ a vertex in its direct neighborhood. Let $\Delta x$, $\Delta y$ and $\Delta z$ be distances defined as:

$$\Delta x = |x_a - x_b|; \Delta y = |y_a - y_b|; \Delta z = |z_a - z_b| \quad (4)$$

Let $\alpha_{min}$, $\alpha_{max}$ and $\beta$ be the controlling parameters for compression, stretching and shearing respectively. Given $x'_a$, $y'_a$, $z'_a$ the new position of A, it is then possible to define the boundary for the valid region:

$$x_{min} = x'_a + (\alpha_{min}\Delta x - \beta(\Delta y + \Delta z)) \quad (5)$$

$$x_{max} = x'_a + (\alpha_{max}\Delta x - \beta(\Delta y + \Delta z)) \quad (6)$$

with $x_{min}$ and $x_{max}$ being the lower and upper corners of the bounding box of the valid region respectively. Similar expressions can be derived for the other two coordinates. If B lies within the region, then there is no change made and we move on to other candidates in the neighborhood. If B lies outside the region, it is moved to the nearest point within the region and its other neighbors are added to the candidate list. The ChainMail propagation is then followed by the relaxation step, in which each element is locally re-positioned so as to be equidistant from its neighbors and the energy of the configuration is minimized. The algorithm is efficient because each element in the volume is considered at most once for each deformation and each element is compared to only one neighbor to determine if and how it must be moved. Furthermore, the mesh of the point elements can be extended to arbitrary grids in 2D and 3D, including triangular and tetrahedral meshes, allowing much greater flexibility in the arrangement of the elements.

The ChainMail algorithm has to be adapted for the deformation of the diaphragm and lung because it requires one initial element be moved in order to start the deformation process and in reality the surface of diaphragm moves simultaneously. The ChainMail algorithm can be modified so that if all the elements are moved simultaneously, the induced deformation is equivalent to that when the elements are moved sequentially one after another.

The final deformation can be obtained by an appropriate weighted average (e.g., by some distance measure between the initial element and the element of interest) of the induced motion from all the elements.

Another modification of the ChainMail algorithm that has to be made is the issue of organ linking. The motion of the lung (and diaphragm) is not only influenced by the contraction of muscles but also governed by ribs because it is attached to the spine and the lower ribs, and therefore its lateral exteriors have to conform to the rib cage. The solution is to link together the areas that are common to two adjacent organs. The vertices at the linked regions are then moved simultaneously. This approach requires a preprocessing step to identify candidate linked regions whose distance must be below a given threshold. The threshold varies depending on the organs, e.g., very small for the diaphragm and liver, around the same value as the fat tissue thickness for the ribs and skin. The organs that are linked together are: diaphragm to the lower ribs, lungs to the upper ribs and diaphragm, external skin to the ribs and sternum.

With the above adaptation of the 3D ChainMail algorithm, a deformable lung model is obtained that is both physically and physiologically plausible. The algorithm is capable of determining the motion of each point element in the lung, including the tumor itself. Owing to the special features of the ChainMail algorithm, this can be done accurately and efficiently.

The second embodiment of the present invention will now be described. The miniature Doppler radar sensor has been used for applications such as physiological measurement [42], microwave interferometry [40] and structural health monitoring [29]. With either direct- or indirect-conversion architectures, the radar suffers from DC offset at the RF front-end output, which may saturate the following stages of baseband amplifiers. In radar sensor applications, the DC offset is mainly caused by the reflections from stationary objects around the target, which is difficult to deal with since it depends on different test environments, and circuit imperfections such as the self-mixing of LO and interferers [41]. To overcome this demerit, AC coupling has been commonly used in such radar sensors. However, AC coupling causes significant signal distortion when the target motion has a very low frequency or a DC component, owing to the highpass characteristics of the coupling capacitor. This is a problem in Doppler radar motion sensing when a target has stationary moment. To deal with it, researchers have proposed several approaches to employ DC coupling in radar sensors. In [43] a method was proposed for calibrating the DC offset while preserving the DC information. However, extra effort is demanded before real time measurement. In [34], low DC offset was achieved using mixers with high LO-RF isolation. However, this method only alleviates the DC offset from circuit imperfection, and the remaining DC offset due to reflection from stationary objects still limits the dynamic range of the baseband amplifiers. In this Letter, we propose a DC coupled CW radar sensor using a fine-tuning adaptive feedback loop technique. The radar output is first fed into a laptop, which then extracts the DC offset information and adaptively adjusts amplifier bias to a level that allows high gain amplification at the baseband stage. The fine-tuning feature also allows the radar sensor to work with the largest dynamic range and be able to detect movement with stationary moment.

Referring now to FIG. 12, an experimental setup 1200 for a radar sensor 122 in accordance with another embodiment of the present invention is shown. The radar sensor 122, with direct-conversion quadrature architecture, is DC-coupled between the RF output and baseband amplifier 414. The I/Q channel baseband outputs are digitized by a data acquisition module 416 (NI-USB6009) that connects to a laptop 120 via a USB port. Through the GPIB interface, the laptop 120 controls a power supply 1202 (Tektronics PS2521G) that is able to sweep over a wide range of voltages. Unlike the conventional AC coupled radar sensor, as shown in the inset where the amplifier is biased at a fixed DC point, the DC coupled radar sensor 122 allows the external power supply 1202 to adjust the biasing level at the baseband amplifier 414. Take the Q channel for example, assuming that the amplifier has infinite open-loop gain, the DC level of the amplifier output is:

$$V_{Q\_OUT} = V_{T\_Q} + \frac{R2}{R1} \cdot (V_Q^+ - V_Q^-) \tag{7}$$

where $V_{T\_Q}$ is the tuning voltage from the power supply, $V_Q^+$ and $V_Q^-$ are the DC offsets of the differential channels, and R2/R1 is the closed-loop gain. In radar sensor applications, a large gain is desired in order to boost the incoming signal that is usually very weak. Due to the reflections from stationary objects and circuit imperfection, the DC difference ($V_Q^+ - V_Q^-$) is not equal to zero. Therefore, with a high gain, even a small difference between the incoming differential signals would be significantly amplified. That is, the second term in (1) is very large. If $V_{T\_Q}$ is fixed at a point, the amplified DC offset could easily saturate the amplifier. For example, if the amplifier power supply is 3.3 V, R2/R1 is set to be 200, ($V_Q^+ - V_Q^-$) DC component is 0.05 V, and $V_{T\_Q}$ is fixed at 1.65 V, the calculated $V_Q$ out DC component reaches at 11.65 V, which is way above the amplifier power supply of 3.3 V. For the DC coupled radar sensor 122, the amplifier output $V_Q$ out is dynamically read by the laptop. Depending on the DC value of $V_Q$ out, the laptop 120 configures the power supply 1202 to increase $V_{T\_Q}$ when the output is close to the lower rail, or decrease $V_{T\_Q}$ when the output is close to the upper rail. This process continues until the amplifier output reaches the desired DC level that allows sufficient high gain but without saturation. Thus, an adaptive feedback loop is formed. Moreover, the power supply's high resolution of 0.01 V makes it possible to fine tune the amplifier output to locate at the middle between the power supply rails, so as to reach the largest dynamic range. Because the tuned DC level can be easily compensated back in software before further signal processing, the DC information is not lost in this solution.

A motion phantom from Varian Medical Systems was placed on the desk. The phantom exhibits sinusoidal-like 0.5 Hz motion but with a short stationary period during the cycle. Three radar sensors similar to the one in [29] but with different baseband circuit structures, were used in the experiments: (1) DC coupled; (2) 10 mF AC coupled; and (3) 30 mF AC coupled. The radar sensor was hung on a metal frame, with its antennas facing the phantom from about 0.5 m away. A camera was placed one meter away from the phantom to record the motion of the phantom. The recorded video was processed to extract the phantom motion, which was then used as a reference to compare with the signal measured by the radar sensor. A software-configured interface programmed in C# was applied to communicate via GPIB with the power supply and control its sweep steps and intervals.

Two sets of experiments were carried out to verify the system performance. Experiment 1: The adaptive feedback loop was tested for its ability to fine-tune the DC offset level. $V_{T\_Q}$ and $V_{T\_I}$ were originally set to be 1.65 V. After reading the I/Q amplifiers' outputs, the laptop sets a negative step to tune the upper curve down and a positive step to tune the lower curve up. The tuning process continues until the amplifier output was tuned to the desired level. To verify the system's ability to relieve from saturation, the radar sensor measured the phantom motion for both cases with and without DC tuning. Experiment 2: The camera and the three radar sensors, as mentioned above, were used to measure the same phantom motion. This test was to verify the system is able to maintain DC information in the measured movement while the AC coupled systems have signal distortion.

Figure 13C:
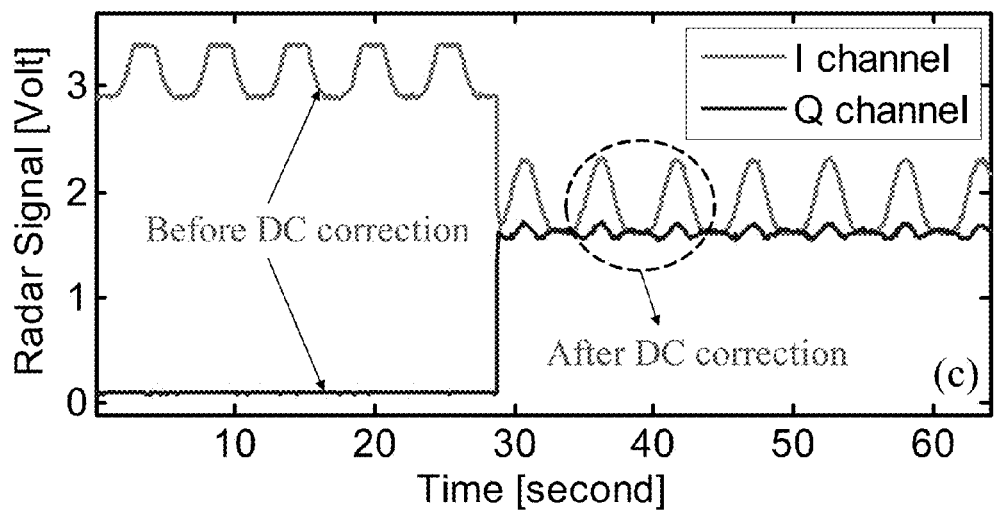
Figure 14:
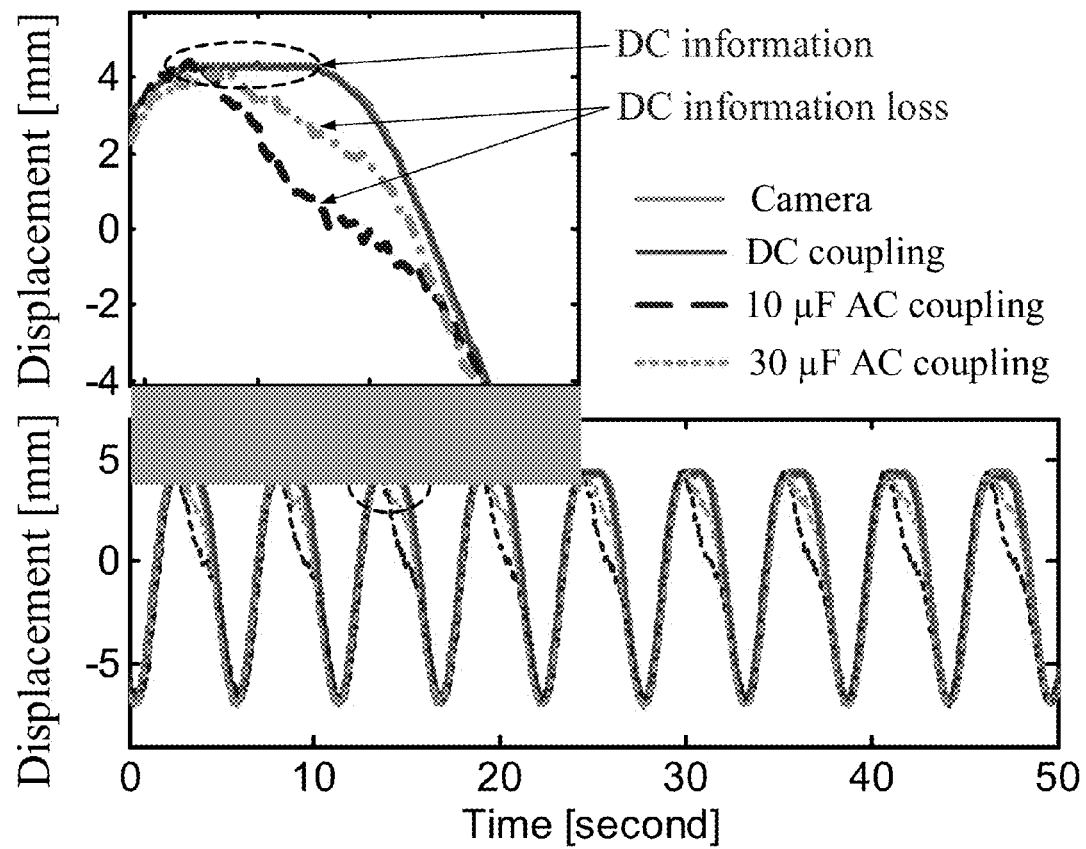
FIG. 14 is a graph showing the measured data of camera, DC coupled radar sensor and AC coupled radar sensors using the circuit shown in FIG. 12.

The experimental results are shown in FIGS. 13 and 14. In FIG. 13A, the shaded area on the left side shows the I channel was originally at the upper end and the Q channel was near the lower end. However, after DC tuning with steps of 0.5 V/0.8 V, respectively, both channels were successfully adjusted step-by-step to a reasonable level, shown as the shaded area on the right side. FIG. 13B shows DC tuning with a finer step of 0.05 V, which allows precisely tuning to half of the amplifier power supply voltage. Therefore, the radar sensor is able to work with the largest dynamic range and maximum signal swing. It should be noted that in a real application, the tuning procedure can be made very fast. FIG. 13C shows the radar measurement results before and after a fast DC tuning. It is seen that the amplifier was originally affected by large DC offset such that the I channel was saturated on the top and the Q channel was totally clamped on the bottom. However, after DC tuning, both channels exhibit satisfactory amplification to signals. The I/Q channels have different amplitudes because of the different residual phase [42]. FIG. 14 illustrates the comparison results for the camera and three radar sensors measuring a movement with stationary moment. After the I/Q signals were recorded, the microwave interferometry method was used to recover the displacement information [40]. It is clearly seen that the displacement measured by the DC coupled sensor matches very well with the reference displacement measured by the camera. On the other hand, both AC coupled radar sensors lead to distortion in the measured displacement, where the DC information is lost. This is because for the stationary situation, the capacitor cannot hold the charge for a long time and tends to charge or discharge. It is also seen that larger capacitors do help alleviate the signal distortion due to lower cutoff frequency. But larger capacitors also result in longer phase delay and system settling time, which may be unacceptable in radar sensor applications.

The third embodiment of the present invention will now be described. FIG. 15 shows the block diagram of the DC coupled radar sensor system 1500 with RF coarse-tuning 1502 and baseband fine-tuning 1504 architectures in accordance with yet another embodiment of the present invention. The radar sensor 1500 was designed with homodyne direct conversion architecture. In radar applications, DC offset occurs at the RF output, which may saturate the amplifiers in the following baseband stages or limit their dynamic range performance. The DC offset mainly comes from: 1) direct coupling from transmitter to receiver and the reflections from stationary objects around the patient, which is difficult to deal with since it depends on different patients and different test environments, and 2) circuit imperfections such as the self-mixing of LO and interferers [41]. As shown in FIG. 15, capacitors 1506 have been commonly placed between the RF output and baseband amplifiers for AC coupling to remove the DC offset. However, the high-pass characteristics of the coupling capacitor lead to significant signal distortion when the target motion has a very low frequency or a DC component. Respiration is a motion that is very low frequency and contains a short period of stationary moment after the lung deflation. So there is practical need for the radar sensor to be able to accurately measure breathing motion with DC coupling.

The designed DC coupled radar sensor 122 eliminates the use of coupling capacitors by employing DC tuning architectures that not only allow the baseband amplifiers 414 to work with sufficient high gain but also preserve the stationary DC information. An RF coarse-tuning signal path 1502 was added at the RF front end of the radar sensor 122 to remove most of the DC offset, and a baseband fine tuning feedback patch 1504 was used to calibrate the remaining DC offset and reach the largest dynamic range. The RF coarse-tuning path 1502 consists of a voltage-controlled attenuator 1508 and a voltage-controlled phase shifter 1510. It collects a portion of the transmitter (Tx) signal and adds it to the receiver (Rx) signal. In this way, by properly tuning the attenuator 1508 and the phase shifter 1510, the signals directly coupled from Tx to Rx and bounced back from the stationary objects were cancelled out [35]. Therefore, the DC offset at the mixer output was greatly reduced. However, due to circuit imperfections, the phase variety of the received signals and the limited resolution of the attenuator 1508 and phase shifter 1510, the feedback path at the RF front end cannot completely remove all the DC offsets, which limits the dynamic range of the baseband amplifiers 414. To deal with this problem, a baseband fine-tuning architecture 1504 was added to adaptively adjust amplifier bias to a level that allows both high gain amplification and maximum dynamic range.

Unlike the conventional AC coupled radar sensor biased at a fixed DC point, the baseband fine-tuning architecture 1504 allows the external power supply or a digital-to-analog converter to adjust the biasing level at the baseband amplifier 414. The radar sensor 122 transmits a single-tone continuous wave (CW) signal T(t) to the target person:

$$T(t) = \cos(2\pi ft + \phi(t)) \quad (8)$$

where the transmitting frequency is f, t is the elapsed time, and ϕ(t) is the phase noise of the oscillator. If this signal is reflected by the chest wall of the target person at a nominal distance d0 with a time-varying displacement given by x(t), the total distance traveled between the transmitter and receiver is $2d(t) = 2d_0 + 2x(t)$. Therefore, the received signal can be approximated as $$R(t) = \cos\left[2\pi ft - \frac{4\pi d_0}{\lambda} - \frac{4\pi x(t)}{\lambda} + \phi\left(t - \frac{4d_0}{c}\right)\right] \quad (9)$$

where c is the signal's propagation velocity (the speed of light), and $\lambda$ is the signal's wavelength in air, which equals to c/f. The received signal is amplified and then down-converted to baseband I/Q differential outputs:

$$V_I^- = V(t)_I^- = -A_I \cos[\theta + 4\pi x(t)/\lambda + \Delta\phi(t)] + DC_I^- \quad (10)$$

$$V_I^+ = V(t)_I^+ = A_I \cos[\theta + 4\pi x(t)/\lambda + \Delta\phi(t)] + DC_I^+ \quad (11)$$

$$V_Q^- = V(t)_Q^- = -A_Q \cos[\theta + 4\pi x(t)/\lambda + \Delta\phi(t)] + DC_Q^- \quad (12)$$

$$V_Q^+ = V(t)_Q^+ = A_Q \cos[\theta + 4\pi x(t)/\lambda + \Delta\phi(t)] + DC_Q^+ \quad (13)$$

where $\theta$ is constant phase offset determined by the initial position of the patient, x(t) is the breathing motion, $\phi(t)$ is the residual phase noise, $A_I/A_Q$ are the amplitudes and $DC_I/DC_Q$ are the DC offsets of the I/Q channels respectively.

The baseband amplifiers' outputs $V_{Q\_OUT}/V_{I\_OUT}$ are dynamically read by the microcontroller 416 (TI MSP430) that transmits the digitized data via a ZigBee node 1512a to another node 1512b connected to the laptop 120. Take the Q channel for example, assuming that the amplifier has infinite open-loop gain, the DC level of the amplifier output is provided by Equation (7) above where $V_{T\_Q}$ is the tuning voltage from the power supply, $V_Q^+$ and $V_Q^-$ are the DC offsets of the differential channels, and R2/R1 is the closed-loop gain. Depending on the DC value of $V_{Q\_OUT}/V_{I\_OUT}$, the laptop 120 configures the power supply (Tektronics PS2521G), through a GPIB interface, to increase the biasing voltage $V_{T\_Q}/V_{T\_I}$ when the output is close to the lower rail, or decrease it when the output is close to the upper rail. This process continues until the amplifier output reaches the desired DC level that allows both high-gain application and maximum dynamic range. The GPIB interface can be removed after the DC tuning process is finished. A wireless tuning loop is also possible by using the ZigBee communications.

Experiments were carried out to validate the DC calibration capability of the DC coupled radar sensor 122. In the first experiment, the RF coarse-tuning loop 1502 was verified to remove most of the DC offset and relieve the voltage level for the baseband fine-tuning 1504. As shown in FIG. 16, the original DC difference of the differential Q channel at the mixer output was 0.07 V. Assume that the baseband amplifier 414 works with a gain of 200, which is necessary to boost the radar signals that are usually very weak, the amplifier DC output results in 14 V, which saturates the amplifier since the DC level is actually way above the amplifier power supply of 3.3 V. To adjust it to half of the power supply, baseband fine-tuning would need $V_{T\_Q}=-12.35$ V DC to be applied to the amplifier, as shown in Equation (7). The high tuning voltage may potentially damage the baseband amplifier 414. However, after RF coarse-tuning, the DC difference drops significantly to 0.005 V. In this case, the baseband fine-tuning only needs $V_{T\_Q}=0.65$ V DC to pull the amplifier DC output to the desired level. In the second experiment, the two tuning architectures were combined to validate the DC calibration functionality.

FIG. 17 shows the DC offset tuning process. It is seen that both I/Q channels were originally at the lower end of the amplifier power supply rails. The coarse-tuning architecture was used to adaptively pull up the I/Q channels step-by-step to reasonable levels that allow further baseband fine tuning. It should be known that the RF output I/Q channels are 90 degrees out of phase, and the coarse-tuning cannot compensate for the phase offset for both channels at the same time. After coarse-tuning, the fine-tuning feedback loop precisely adjusts the I/Q DC offsets to the desired levels, with a fine step of 0.01 V, owing to the high resolution of the power supply. In FIG. 17, the baseband amplifiers' outputs were precisely tuned to 1.65 V, which is half way between the baseband amplifier supply rails, so that the maximum dynamic range is guaranteed. It should be noted that in real application, the tuning procedure can be made very fast (within a few milliseconds).

Figure 18:
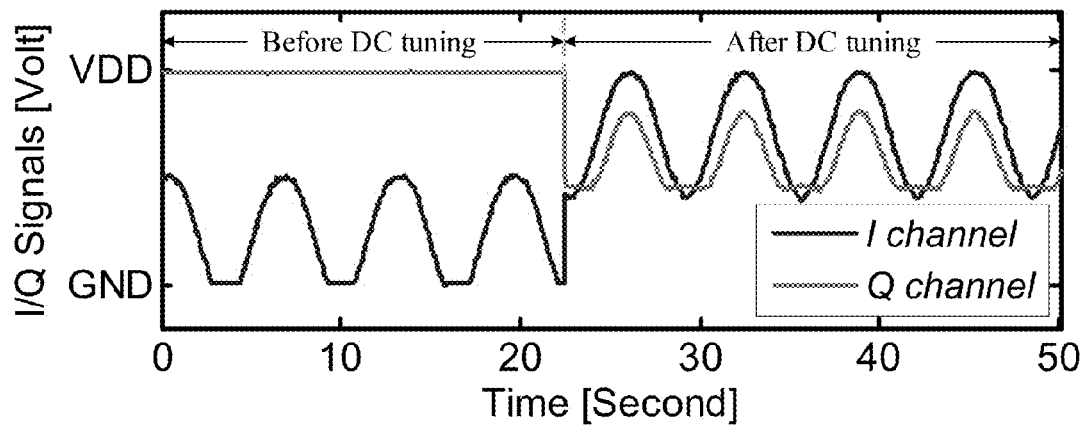
FIG. 18 is a graph showing the radar measurement result before and after DC tuning using the circuit shown in FIG. 15.

FIG. 18 shows the radar measurement results before and after a fast DC tuning. It is seen that the amplifier was originally affected by large DC offset such that the Q channel was totally saturated on the top and the I channel was partially clamped on the bottom. However, after DC tuning, both channels exhibit satisfactory amplification on signals. The I/Q channels have different amplitudes due to the different residual phase [42].

Figure 19:
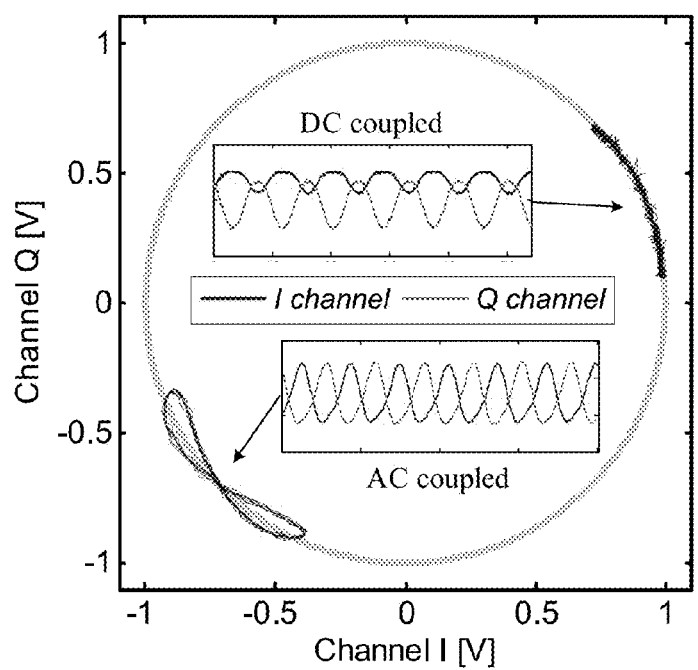
FIG. 19 is a graph showing the constellation graph of the signals measured by AC radar and DC radar using the circuit shown in FIG. 15.

The DC coupled radar sensor 122 is able to measure target motions with stationary moment. That is, it can preserve the DC information of the stationary moment. It can also preserve the DC information that comes from the nonlinear cosine expansion, which is necessary for accurate arctangent demodulation. In a word, owing to the all-pass characteristic of the DC coupled structure, the radar sensor 122 is able to maintain the signal integrity by preserving all the DC information. In FIG. 19, the AC coupled radar and the DC coupled radar were used to measure the same sinusoidal motion of an actuator. The measurement results are shown in a constellation graph to compare the I/Q trajectories. It is seen that the trajectory of the DC coupled radar matches well with the unit circle, while the AC coupled radar tends to deviate from the circular arc to form a ribbon-like shape. This is because of the radar signal amplitude variation that is caused by the AC coupling capacitors' charging and discharging. Since the DC coupled radar has a trajectory that is much closer to an ideal arc, it can be used for more accurate DC calibration [43], and therefore leads to more accurate arctangent demodulation.

To verify the DC coupled radar's ability to preserve the DC information of stationary moment, both the DC radar and AC radar were used to measure the actuator that was programmed to move sinusoidally but with a stationary moment between two adjacent cycles. The measurement results were shown in FIG. 20. It is seen that the DC coupled radar successfully preserves the stationary information by precisely matching with the programmed actuator motion. However, the AC radar measured movement starts to deviate from the ground truth when the stationary moment begins. This is because the AC coupling capacitors cannot hold the charge for a long time and they tend to discharge over the stationary moment. The DC coupled radar sensor 122 is expected to more precisely measure the respiration motion that is very low frequency and has a short stationary moment during its cycle.

The accuracy of the DC coupled radar sensor 122 for respiration measurement has been evaluated with physical experiments in a radiotherapy environment. During the experiments, the radar sensor 122 was placed on the fixation frame crossed over the treatment platform, as shown in FIGS. 21A-21C. The respiration data were wirelessly transmitted to a ZigBee receiver end connected to the laptop that was placed outside the treatment room.

Three experiments were carried out to validate the use of radar respiration sensing for clinical applications in radiotherapy. First, a physical motion phantom performed a sinusoidal-like movement with a ~5-s period during each cycle.

The radar sensor 122 and the Real-time Position Management (RPM) system (Varian Medical Systems, Palo Alto, Calif.) were used to measure the same motion phantom on the treatment platform. The RPM system is a widely used respiration monitoring approach in radiotherapy, which employs an infrared camera to track an external reflective marker put on the patient's chest or abdomen. An infrared marker was put on top of the phantom in order for the RPM system to track its motion. The infrared camera was mounted on the wall and is in the line of sight of the marker. This experiment evaluated the accuracy performance of the radar sensor 122. The setup of this test is shown in FIG. 21A. To simulate the real clinical situation, the treatment radiation was turned on during the phantom test. Under some ideal situations, the RPM system using an infrared camera and reflective marker can provide accurate measurement of respiratory signal of a single point, and thus was used as the gold standard to assess the performance of the radar sensor 122. However, because of the complexity of human respiration, the internal tumor location cannot be derived from only a point measurement with sufficient accuracy. This requires simultaneous measurement of multiple external surrogates, which can be achieved by the radar system. In the second experiment, a human subject laid on the treatment platform to simulate the patient's respiration. The setup is shown in FIG. 21B. In the third experiment, to further account for the clinically relevant breathing patterns, the Respiratory Gating Platform (Standard Imaging, Middleton, Wis.) was used to simulate breathing motions with various amplitudes and periods. The Respiratory Gating Platform simulates breathing motions for training, quality assurance and dose verification in radiotherapy. Radar measured the different motion patterns during the experiment. The setup is shown in FIG. 21C.

The measurement results are illustrated in FIG. 22 for the phantom case. It is seen that the radar sensor measurement matches very well with that from the RPM system. This demonstrates that the radar sensor 122 is not interfered by the high-energy radiation dose and can work compatibly with the LINAC during the radiation dose delivery process. For the experiment on the human subject, the radar measured respiration is shown in FIG. 23A. The subject was coached to dynamically adjust his breathing to put the end of expiration (EOE) position within the shaded area, so as to generate reproducible respiration signals, from which, gating signals would be easy to be obtained. The accurate measurement of the DC coupled radar sensor 122 also allows the coaching reference area to be chosen near the position of end of inspiration (EOI), depending on specific clinical situations. The radar sensor 122 measured reproducible respiration signals allow both amplitude gating and phase gating [44]. The red line in FIG. 23A shows the reference for amplitude gating. The respiration signal triggers the radiation on once its amplitude falls below the reference line. FIG. 23B shows the gating signals with a duty cycle of 40.5%.

Figures 24A, 24B, 24C:
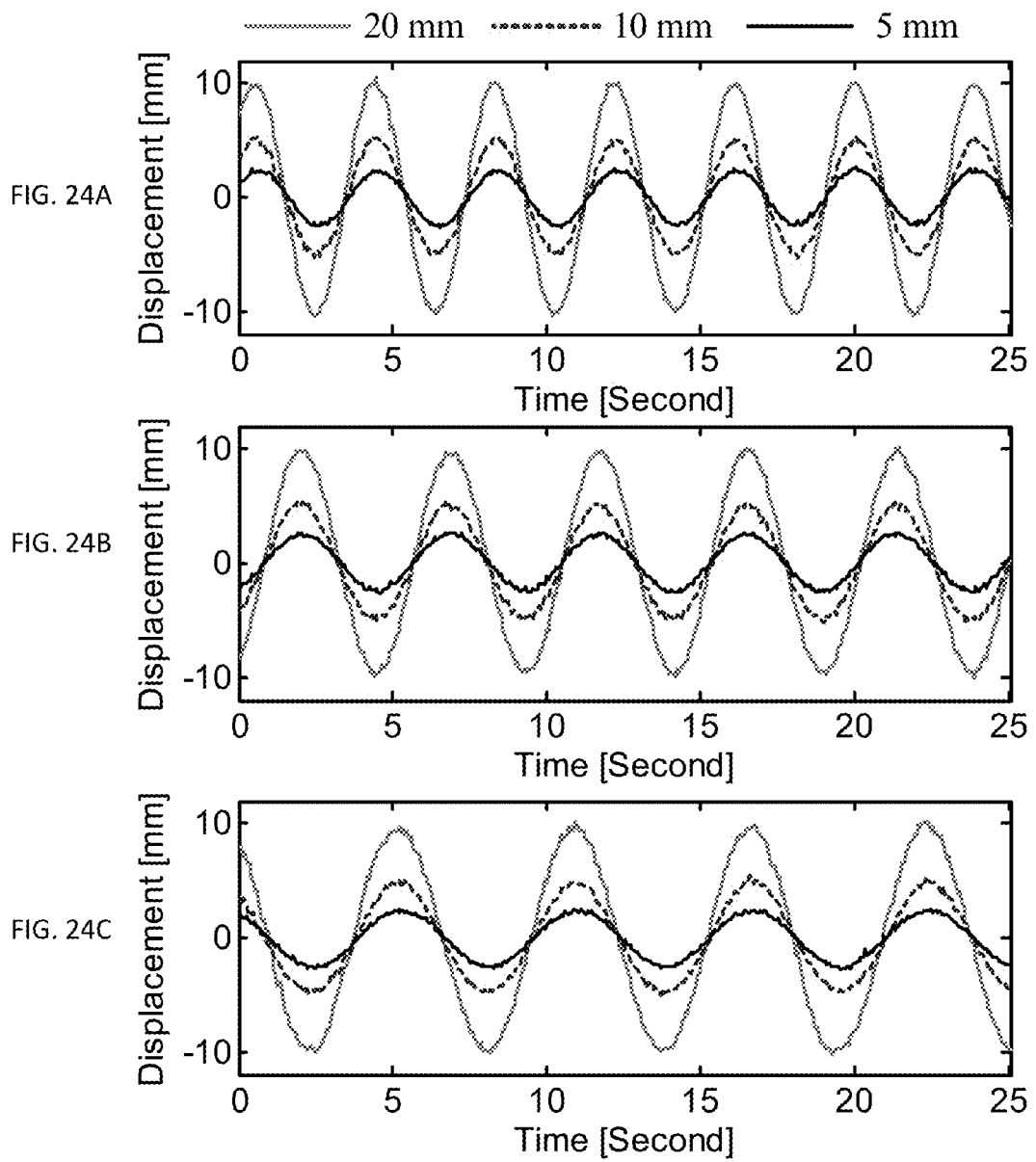
FIGS. 24A-24C are graphs showing radar measured gating platform motions with amplitudes of 20 mm, 10 mm and 5 mm, and periods of 4 seconds (FIG. 24A), (b) 5 seconds (FIG. 24B), and 6 seconds (FIG. 24C).

For the Respiratory Gating Platform measurement, the radar sensor 122 measured data are shown in FIGS. 24A-24C. The platform was configured to move at amplitudes of 5 mm, 10 mm and 20 mm, and with periods of 4 seconds (FIG. 24A), 5 seconds (FIG. 24A) and 6 seconds (FIG. 24A), respectively. These motion patterns represent the common breathing parameters in the clinical radiotherapy. It is seen that the radar sensor was able to accurately capture all the respiration motion patterns with various amplitudes and periods. The radar measurement accuracy for various motion patterns is illustrated in Table 1.

TABLE 1

Accuracy of the Radar Measurement for Various Motion Patterns

| Amplitude [mm] | Period [second] | RMS Err. [mm] |
|---|---|---|
| 20 | 4 | 0.202 |
|  | 5 | 0.209 |
|  | 6 | 0.211 |
| 10 | 4 | 0.176 |
|  | 5 | 0.175 |
|  | 6 | 0.179 |
| 5 | 4 | 0.103 |
|  | 5 | 0.091 |
|  | 6 | 0.115 |

The RMS error was obtained by comparing the radar measured movement with the actual motion pattern of the gating platform. The measurement error is mainly due to the radar system noise, such as quantization noise, electronic noise and environmental noise, which introduces variations to the measured signal. However, even with noise, it is shown that the radar sensor has a sub-mm measurement accuracy.

The DC coupled CW radar sensor 122 in accordance with the present invention provides a non-contact and non-invasive approach for accurate respiration measurement in motion-adaptive radiotherapy. The radar sensor 122 is configured with adaptive DC tuning architectures and able to precisely measure movements with stationary moment, such as the respiration motion. The concept of a radiotherapy system with radar sensing has been introduced and described in the context of respiratory gating and tumor tracking for motion-adaptive radiotherapy. The DC coupled CW radar sensor was designed and its DC tuning capability was tested. Experiments were carried out to validate the radar sensor for measuring movements with stationary moment. The accuracy of respiration measurement using DC coupled radar sensor has been experimentally evaluated using both physical phantom and human subject in a radiotherapy environment. It has been shown that respiration measurement with radar sensor 122 while the radiation beam is on is feasible and the measurement has a sub-mm accuracy when compared with the commercial Respiratory Gating Platform. The radar sensor 122 provides accurate, non-invasive, and non-contact respiration measurement and therefore has a great potential in motion-adaptive radiotherapy.

It will be understood by those of skill in the art that information and signals may be represented using any of a variety of different technologies and techniques (e.g., data, instructions, commands, information, signals, bits, symbols, and chips may be represented by voltages, currents, electromagnetic waves, magnetic fields or particles, optical fields or particles, or any combination thereof). Likewise, the various illustrative logical blocks, modules, circuits, and algorithm steps described herein may be implemented as electronic hardware, computer software, or combinations of both, depending on the application and functionality. Moreover, the various logical blocks, modules, and circuits described herein may be implemented or performed with a general purpose processor (e.g., microprocessor, conventional processor, controller, microcontroller, state machine or combination of computing devices), a digital signal processor ("DSP"), an application specific integrated circuit ("ASIC"), a field programmable gate array ("FPGA") or other programmable logic device, discrete gate or transistor logic, discrete hardware components, or any combination thereof designed to perform the functions described herein. Similarly, steps of a method or process described herein may be embodied directly in hardware, in a software module executed by one or more processors, or in a combination of the two. A software module may reside in RAM memory, flash memory, ROM memory, EPROM memory, EEPROM memory, registers, hard disk, a removable disk, a CD-ROM, or any other form of storage medium known in the art. Although preferred embodiments of the present invention have been described in detail, it will be understood by those skilled in the art that various modifications can be made therein without departing from the spirit and scope of the invention as set forth in the appended claims.

REFERENCES

[1] Keall, P. J., V. R. Kini, S. S. Vedam, and R. Mohan, "Motion adaptive x-ray therapy: a feasibility study," Phys Med Biol, vol. 46, no. 1, pp. 1-10, 2001.

[2] Shirato, H., T. Harada, T. Harabayashi et al., "Feasibility of insertion/implantation of 2.0-mm-diameter gold internal fiducial markers for precise setup and real-time tumor tracking in radiotherapy," Int J Radiat Oncol Biol Phys, vol. 56, no. 1, pp. 240-247, 2003.

[3] Tang, X., G. C. Sharp, and S. B. Jiang, "Fluoroscopic tracking of multiple implanted fiducial markers using multiple object tracking," Phys Med Biol, 2007. 52(14): p. 4081-4098.

[4] Murphy, M. J., "Tracking moving organs in real time," Semin Radiat Oncol, vol. 14, no. 1, pp. 91-100, 2004.

[5] Balter, J. M., J. N. Wright et al., "Accuracy of a wireless localization system for radiotherapy," Int J Radiat Oncol Biol Phys, vol. 61, no. 3, pp. 933-40, 2005.

[6] Shirato, H., S. Shimizu et al., "Physical aspects of a realtime tumor-tracking system for gated radiotherapy," Int J Radiat Oncol Biol Phys, vol. 48, no. 4, pp. 1187-1195, 2000.

[7] Arslan, S., A. Yilmaz, B. Bayramgurler, O. Uzman, E. Nver, and E Akkaya, "CT-guided transthoracic fine needle aspiration of pulmonary lesions: accuracy and complications in 294 patients," Med Sci Monit, vol. 8, no. 7, pp. 493-500, 2002.

[8] Geraghty, P. R., S. T. Kee, et al., "CT-guided transthoracic needle aspiration biopsy of pulmonary nodules: needle size and pneumothorax rate," Radiology, 2003. 229(2): p. 475-481.

[9] Cui, Y., J. G. Dy, G. C. Sharp, B. Alexander, and S. B. Jiang, "Multiple template-based fluoroscopic tracking of lung tumor mass without implanted fiducial markers," Phys Med Biol, vol. 52, no. 20, pp. 6229-6242, 2007.

[10] Xu, Q., R. J. Hamilton, R. A. Schowengerdt, B. Alexander, and S. B. Jiang, "Lung Tumor Tracking in Fluoroscopic Video Based on Optical Flow," Medical Physics, vol. 35, no. 12, pp. 5351-5359, 2008.

[11] Xu, Q., R. J. Hamilton, R. A. Schowengerdt, and S. B. Jiang, "A deformable lung tumor tracking method in fluoroscopic video using active shape models: a feasibility study," Phys Med Biol, vol. 52, no. 17, pp. 5277-5293, 2007.

[12] Lin, T., L. I. Cervino, X. Tang, N. Vasconcelos, and S. B. Jiang, "Fluoroscopic tumor tracking for image-guided lung cancer radiotherapy," Phys Med Biol, vol. 54, no. 4, pp. 981-992, 2009.

[13] Shope, T. B., "Radiation-induced skin injuries from fluoroscopy," Radiographics, vol. 16, no. 5, pp. 1195-1199, 1996.

[14] Ron, E., "Ionizing radiation and cancer risk: Evidence from epidemiology." Radiation Research, vol. 150, no. 5, pp. S30-S41, 1998.

[15] Jiang, S. B., "Technical aspects of image-guided respirationgated radiation therapy," Med Dosim, vol. 31, no. 2, pp. 141-151, 2006.

[16] Kubo, H. D., P. M. Len, S. Minohara, and H. Mostafavi, "Breathing-synchronized radiotherapy program at the University of California Davis Cancer Center," Med Phys, vol. 27, no. 2, pp. 346-353, 2000.

[17] Wong, J. W., M. B. Sharpe et al., "The use of active breathing control (ABC) to reduce margin for breathing motion," Int J Radiat Oncol Biol Phys, vol. 44, no. 4, pp. 911-920, 1999.

[18] Bert, C., K. G. Metheany, K. Doppke, and G. T. Chen, "A phantom evaluation of a stereo-vision surface imaging system for radiotherapy patient setup," Med Phys, vol. 32, no. 9, pp. 2753-2762, 2005.

[19] C. Li J. Cummings, J. Lam, E. Graves, W. Wu, "Radar remote monitoring of vital signs," IEEE Microwave Magazine, vol. 10, issue 1, pp. 47-56, February 2009.

[20] K. M. Chen, D. Misra, H. Wang, H. R. Chuang, and E. Postow, "An X-band microwave life-detection system," IEEE Trans. Biomedical Engineering, vol. 33, pp. 697-702, July 1986.

[21] J. C. Lin, "Microwave sensing of physiological movement and volume change: A review," Bioelectromagnetics, vol. 13, pp. 557-565, 1992.

[22] C. Gu, C. Li, J. Lin, J. Long, J. T. Huangfu, L. Ran, "Instrument-based noncontact Doppler radar vital sign detection system using heterodyne digital quadrature demodulation architecture," IEEE Transactions on Instrumentation and Measurement, vol. 59, no. 6, pp. 1580-1588, 2010.

[23] C. Li, X. Yu, C. Lee, D. Li, L. Ran, J. Lin, "High-sensitivity software-configurable 5.8-GHz radar sensor receiver chip in 0.13-um CMOS for noncontact vital sign detection," IEEE Transactions on Microwave Theory and Techniques, vol. 58, no. 5, 2010.

[24] Wilson, T. A., A. Legrand, P. A. Gevenois, and A. DeTroyer, "Respiratory effects of the external and internal intercostal muscles in humans," J Physiol, vol. 530, pp. 319-349, 2001.

[25] Gibson, S. F., "3D chainmail: a fast algorithm for deforming volumetric objects, in Proceedings of the 1997 symposium on Interactive 3D graphics," ACM: Providence, R.I., 1997.

[26] Rice, J. A., Li, C., Gu, C., and Hernandez, J. C., "A wireless multifunctional radar-based displacement sensor for structural health monitoring," SPIE Smart Structures/NDE 2010, San Diego, Calif., USA, March 2011.

[27] S. B. Jiang, "Radiotherapy of mobile tumors," Seminars in Radiation Oncology, Vol. 16, Issue. 4, pp. 239-24, October 2006.

[28] S. B. Jiang, "Technical aspects of image-guided respiration gated radiation therapy," Medical Dosimetry, Vol. 31 (2), pp. 141-151, 2006.

[29] C. Gu, R. Li, C. Li, and S. B. Jiang, "A multi-radar wireless system for respiratory gating and accurate tumor tracking in lung cancer radiotherapy", 33rd Annual International Conference of the IEEE Engineering in Medicine and Biology Society (EMBC '11), Boston Mass., August 2011.

[30] F. Laurent, V. Latrabe, B. Vergier, M. Montaudon, J. Vernejoux and J. Dubrez, "CT-guided transthoracic needle biopsy of pulmonary nodules smaller than 20 mm results with an automated 20-gauge coaxial cutting needle", Clin. Radiol. Vol. 55, pp. 281-287, 2000.

[31] C. Li, C. Gu, R. Li, and S. B. Jiang, "Radar Motion Sensing for Accurate Tumor Tracking in Radiation

[32] J. C. Lin, "Noninvasive microwave measurement of respiration", Proceedings of the IEEE, Vol. 63, No. 10, pp. 1530-1530, October 1975.

[33] J. C. Lin, "Noninvasive and remote wireless sensing of physiologic signatures and vital signals", XVII Argentinean Congress on Bioengineering, Rosario, Argentina. October 2009.

[34] X. Zhao, C. Song, O. Boric-Lubecke, and V. M. Lubecke, "DC Coupled Doppler Radar Physiological Monitor", 33rd Annual International Conference of the IEEE Engineering in Medicine and Biology Society (EMBC '11), Boston Mass., August 2011.

[35] I. Mostafanezhad, and O. Boric-Lubecke, "An RF Based Analog Linear Demodulator", IEEE Microwave and Wireless Components Letters, Vol. 21, No. 7, pp 392-394, July 2011.

[36] W. Pan, J. Wang, J. Huangfu, C. Li, and L. Ran, "Null point elimination using RF phase shifter in continuous wave Doppler radar system," Electronics Letter, vol. 47, no. 21, p. 1196-1198, October 2011.

[37] R. I. Berbeco, S. Nishioka, H. Shirato, and S. B. Jiang, "Residual motion of lung tumors in end-of-inhale respiratory gated radiotherapy based on external surrogates", Med. Phys. Vol. 33, No. 11, 2006.

[38] H. Yan, F. Yin, G. Zhu, M. Ajlouni, and J. Kim, "The correlation evaluation of a tumor tracking system using multiple external markers", Med Phys, 2006. 33(11): 4073-84.

[39] C. Gu, Z. Salmani, H. Zhang, and C. Li, "Antenna Array Technology for Radar Respiration Measurement in Motion-adaptive Lung Cancer Radiotherapy", IEEE Radio and Wireless Week, Santa Clara Calif., January 2012.

[40] S. Kim, and C. Nguyen, "A displacement measurement technique using millimeter-wave interferometry," IEEE Trans. Microwave Theory and Techniques, Vol. 51, No. 6, pp. 1724-1728, 2003.

[41] B. Razavi, "Design Considerations for Direct-Conversion Receivers", IEEE Trans. Circuits & Systems I, Vol. 44, No. 6, pp 428-435, June 1997.

[42] A. D. Droitcour, O. Boric-Lubecke, V. M. Lubecke, J. Lin, and G. T. A. Kovac, "Range correlation and I/Q performance benefits in single-chip silicon Doppler radars for noncontact cardiopulmonary monitoring," IEEE Trans. Microwave Theory and Techniques, Vol. 52, No. 3, pp. 838-848, March 2004.

[43] B. K. Park, O. Boric-Lubecke, and V. M. Lubecke, "Arctangent demodulation with DC offset compensation in quadrature Doppler radar receiver systems," IEEE Trans. Microwave Theory and Techniques, Vol. 55, No. 5, pp. 1073-1079, May 2007.

[44] C. Gu, R. Li, C. Li, and S. B. Jiang, "Doppler Radar Respiration Measurement for Gated Lung Cancer Radiotherapy", IEEE Radio and Wireless Week, Phoenix Ariz., January 2011.

[45] K. Mostov, and E. Liptsen, "Medical Applications of Shortwave RM Radar: Remote Monitoring of Cardiac and Respiratory Motion," Medical Physics Online Journal, March 2010.

What is claimed is:

1. A method for controlling a treatment device comprising the steps of:
(a) providing a radar sensor comprising: (i) a microwave signal source, (ii) a first amplifier connected to the microwave signal source, (iii) one or more transmitting antennas connected to the first amplifier, (iv) one or more receiver antennas, (e) a second amplifier connected to the one or more receiver antennas, (v) a DC offset course-tuning circuit connected to the one or more transmitter antennas and the one or more receiver antennas, (vi) a signal mixer connected to the microwave signal source and the second amplifier, (vii) a DC coupling circuit connected to the signal mixer, (viii) a baseband amplifier connected to the DC coupling circuit, (ix) a DC offset fine-tuning circuit connected to the baseband amplifier, and (x) one or more processors connected to the baseband amplifier, the DC offset course-tuning circuit and the DC offset fine-tuning circuit;
(b) generating a microwave signal;
(c) radiating the microwave signal to a subject;
(d) receiving a modulated microwave signal from the subject;
(e) processing the modulated microwave signal to provide a subject motion information using an arctangent-demodulation microwave interferometry mode;
(f) determining a location of a target on or within the subject based on the subject motion information and a three-dimensional model for the subject and the target;
(g) generating one or more control signals based on the location of the target;
(h) controlling the treatment device using the one or more control signals to treat the target on or within the subject; and
wherein steps (b)-(h) are performed using the radar sensor.

2. The method as recited in claim 1, wherein the treatment device comprises a radiation beam device or a laser.

3. The method as recited in claim 1, wherein the subject is a human or an animal.

4. The method as recited in claim 1, wherein the target comprises a tumor, a growth, a tissue, or a skin cancer.

5. The method as recited in claim 1, wherein the subject motion information comprises a chest wall motion information and an abdomen motion information.

6. The method as recited in claim 1, wherein the subject motion information and the three-dimensional model for the subject and the target are used to determine an exact location of the target on or within the subject.

7. The method as recited in claim 1, wherein the one or more control signals start and stop a beam of the treatment device or steer the beam of the treatment device.

8. The method as recited in claim 7, wherein the beam comprises an electron beam, a gamma beam, a photon beam, a proton beam or an X-ray beam.

9. The method as recited in claim 1, wherein all the steps are performed in real-time.

10. The method as recited in claim 1, further comprising the steps of:
scanning the subject and the target to collect a subject and target geometrical information; and
generating the three-dimensional model for the subject and the target based on the subject and target geometrical information.

11. The method as recited in claim 10, wherein the scanning step is performed using a computed tomography device, a magnetic resonance imaging device, a magnetic resonance tomography device, a positron emission tomography device, a single photon emission computed tomography device or an ultrasound device.

12. The method as recited in claim 1, wherein the three-dimensional model also includes one or more organs.

13. The method as recited in claim 1, further comprising the step of designing a treatment plan for the subject using the three-dimensional model.

14. The method as recited in claim 1, wherein the arctangent-demodulation microwave interferometry mode provides the subject motion information by demodulating the modulated microwave signal using $\psi(t)=\tan^{-1}[B(t)_Q/B(t)_I]+F=\theta+4\pi x(t)/\lambda+\Delta\phi(t)$.

15. The method as recited in claim 1, further comprising the step of providing a DC offset calibration.

16. The method as recited in claim 15, wherein the DC offset calibration produces an I channel defined by $B(t)_I=A_I \cos[\theta+4\pi x(t)/\lambda+\Delta\phi(t)]+DC_I$ and a Q channel defined by $B(t)_Q=A_Q \sin[\theta+4\pi x(t)/\lambda+\Delta\phi(t)]+DC_Q$.

17. The method as recited in claim 1, further comprising the step of adaptively pulling up both an I channel and a Q channel to a specified levels.

18. The method as recited in claim 1, further comprising the step of adjusting both an I channel and a Q channel to a specified levels.

19. The method as recited in claim 1, wherein the DC offset course-tuning circuit comprises:
- a first coupler connected between the first amplifier and the one or more transmitter antennas;
- a second coupler connected between the second amplifier and the one or more receiver antennas; and
- a voltage-controlled attenuator and a voltage-controlled phase shifter connected between the first coupler and the second coupler.

20. A radar sensor comprising:
- a microwave signal source;
- a first amplifier connected to the microwave signal source;
- one or more transmitting antennas connected to the first amplifier;
- one or more receiver antennas;
- a second amplifier connected to the one or more receiver antennas;
- a DC offset course-tuning circuit connected to the one or more transmitter antennas and the one or more receiver antennas;
- a signal mixer connected to the microwave signal source and the second amplifier;
- a DC coupling circuit connected to the signal mixer;
- a baseband amplifier connected to the DC coupling circuit;
- a DC offset fine-tuning circuit connected to the baseband amplifier; and
- one or more processors connected to the baseband amplifier, the DC offset course-tuning circuit and the DC offset fine-tuning circuit, wherein the one or more processors provides an arctangent-demodulation microwave interferometry mode and a subject motion information.

21. The radar sensor as recited in claim 20, wherein the microwave signal source further comprises a low-dropout regulator.

22. The radar sensor as recited in claim 20, wherein the first amplifier comprises a first variable gain amplifier or the second amplifier comprises a second variable gain amplifier.

23. The radar sensor as recited in claim 20, wherein the second amplifier further comprises a signal processor.

24. The radar sensor as recited in claim 20, wherein the arctangent-demodulation microwave interferometry mode provides the subject motion information by demodulating the modulated microwave signal using $\psi(t)=\tan^{-1}[B(t)_Q/B(t)_I]+F=\theta+4\pi x(t)/\lambda+\Delta\phi(t)$.

25. The radar sensor as recited in claim 20, wherein the one or more processors further provide a DC offset calibration using the DC offset fine-tuning circuit.

26. The radar sensor as recited in claim 25, wherein the DC offset calibration produces an I channel defined by $B(t)_I=A_I \cos[\theta+4\pi x(t)/\lambda+\Delta\phi(t)]+DC_I$ and a Q channel defined by $B(t)_Q=A_Q \sin[\theta+4\pi x(t)/\lambda+\Delta\phi(t)]+DC_Q$.

27. The radar sensor as recited in claim 20, wherein the DC offset course-tuning circuit adaptively pulls up both an I channel and a Q channel to a specified levels.

28. The radar sensor as recited in claim 20, wherein the DC offset course-tuning circuit comprises:
- a first coupler connected between the first amplifier and the one or more transmitter antennas;
- a second coupler connected between the second amplifier and the one or more receiver antennas; and
- a voltage-controlled attenuator and a voltage-controlled phase shifter connected between the first coupler and the second coupler.

29. The radar sensor as recited in claim 20, wherein the DC offset fine-tuning circuit adjusts both an I channel DC offset and a Q channel DC offset to a specified levels.

30. The radar sensor as recited in claim 20, wherein the DC offset fine-tuning circuit comprises a level shifter connected to the baseband amplifier and the one or more processors.

31. The radar sensor as recited in claim 20, wherein the microwave signal source generates a single tone continuous wave signal.

32. The radar sensor as recited in claim 20, wherein the one or more transmitting antennas and the one or more receiver antennas are located proximate to one another.

33. The radar sensor as recited in claim 20, wherein the signal mixer provides a set of baseband differential outputs $(V_I^-, V_I^+, V_Q^-, V_Q^+)$ to the DC coupling circuit.

34. The radar sensor as recited in claim 20, wherein the arctangent-demodulation microwave interferometry mode and the subject motion information are used to track a motion of a target.

35. A treatment system comprising:
- a treatment device;
- a radar sensor comprising:
  - a microwave signal source,
  - a first amplifier connected to the microwave signal source,
  - one or more transmitting antennas connected to the first amplifier,
  - one or more receiver antennas,
  - a second amplifier connected to the one or more receiver antennas,
  - a DC offset course-tuning circuit connected to the one or more transmitter antennas and the one or more receiver antennas,
  - a signal mixer connected to the microwave signal source and the second amplifier,
  - a DC coupling circuit connected to the signal mixer,
  - a baseband amplifier connected to the DC coupling circuit,
  - a DC offset fine-tuning circuit connected to the baseband amplifier; and
  - one or more processors connected to the baseband amplifier, the DC offset course-tuning circuit and the DC offset fine-tuning circuit, wherein the one or more processors provides an arctangent-demodulation microwave interferometry mode and a subject motion information; and
- a controller communicably connected to the treatment device and the one or more processors of the radar sensor, wherein the controller determines a location of a target on or within a subject based on the subject motion information and a three-dimensional model for the subject and the target, generates one or more control signals based on the location of the target, and controls the treatment device using the one or more control signals to treat the target on or within the subject.

36. The treatment system as recited in claim 35, wherein the treatment device comprises a radiation beam device or a laser.

37. The treatment system as recited in claim 35, wherein the subject is a human or an animal.

38. The treatment system as recited in claim 35, wherein the target comprises a tumor, a growth, a tissue, or a skin cancer.

39. The treatment system as recited in claim 35, wherein the subject motion information comprises a chest wall motion information and an abdomen motion information.

40. The treatment system as recited in claim 35, wherein the subject motion information and the three-dimensional model for the subject and the target are used to determine an exact location of the target on or within the subject.

41. The treatment system as recited in claim 35, wherein the one or more control signals start and stop a beam of the treatment device or steer the beam of the treatment device.

42. The treatment system as recited in claim 41, wherein the beam comprises an electron beam, a gamma beam, a photon beam, a proton beam or an X-ray beam.

43. The treatment system as recited in claim 35, wherein the controller determines the location of the target, generates the one or more control signals, and controls the treatment device in real-time.

44. The treatment system as recited in claim 35, wherein a subject and target geometrical information is collected by scanning the subject and the target, and the three-dimensional model is generated for the subject and the target based on the subject and target geometrical information.

45. The treatment system as recited in claim 44, wherein the subject and the target are scanned using a computed tomography device, a magnetic resonance imaging device, a magnetic resonance tomography device, a positron emission tomography device, a single photon emission computed tomography device or an ultrasound device.

46. The treatment system as recited in claim 35, wherein the three-dimensional model also includes one or more organs.

47. The treatment system as recited in claim 35, wherein the three-dimensional model is used to design a treatment plan for the subject.

48. The treatment system as recited in claim 35, wherein the microwave signal source further comprises a low-dropout regulator.

49. The treatment system as recited in claim 35, wherein the first amplifier comprises a first variable gain amplifier or the second amplifier comprises a second variable gain amplifier.

50. The treatment system as recited in claim 35, wherein the second amplifier further comprises a signal processor.

51. The treatment system as recited in claim 35, wherein the arctangent-demodulation microwave interferometry mode provides the subject motion information by demodulating the modulated microwave signal using $\psi(t)=\tan^{-1}[B(t)_Q/B(t)_I]+F=\theta+4\pi x(t)/\lambda+\Delta\phi(t)$.

52. The treatment system as recited in claim 35, wherein the one or more processors further provide a DC offset calibration using the DC offset fine-tuning circuit.

53. The treatment system as recited in claim 52, wherein the DC offset calibration produces an I channel defined by $B(t)_I=A_I \cos[\theta+4\pi x(t)/\lambda+\Delta\phi(t)]+DC_I$ and a Q channel defined by $B(t)_Q=A_Q \sin[\theta+4\pi x(t)/\lambda+\Delta\phi(t)]+DC_Q$.

54. The treatment system as recited in claim 35, wherein the DC offset course-tuning circuit adaptively pulls up both an I channel and a Q channel to a specified levels.

55. The treatment system as recited in claim 35, wherein the DC offset course-tuning circuit comprises:
a first coupler connected between the first amplifier and the one or more transmitter antennas;
a second coupler connected between the second amplifier and the one or more receiver antennas; and
a voltage-controlled attenuator and a voltage-controlled phase shifter connected between the first coupler and the second coupler.

56. The treatment system as recited in claim 35, wherein the DC offset fine-tuning circuit adjusts both an I channel DC offset and a Q channel DC offset to a specified levels.

57. The treatment system as recited in claim 35, wherein the DC offset fine-tuning circuit comprises a level shifter connected to the baseband amplifier and the one or more processors.

58. The treatment system as recited in claim 35, wherein the microwave signal source generates a single tone continuous wave signal.

59. The treatment system as recited in claim 35, wherein the one or more transmitting antennas and the one or more receiver antennas are located proximate to one another.

60. The treatment system as recited in claim 35, wherein the signal mixer provides a set of baseband differential outputs $(V_I^-, V_I^+, V_Q^-, V_Q^+)$ to the DC coupling circuit.

61. The treatment system as recited in claim 35, wherein the controller further tracks a motion of the target using the arctangent-demodulation microwave interferometry mode and the subject motion information.

* * * * *